US008784447B2

(12) United States Patent
Coleman et al.

(10) Patent No.: US 8,784,447 B2
(45) Date of Patent: *Jul. 22, 2014

(54) SURGICAL STAPLER

(75) Inventors: James Coleman, Terenure (IE); Christy Cummins, Naas (IE); Chris Martin, Dublin (IE); Thomas Raymond Anthony, Rathfarnham (IE); Sean Morris, Athlone (IE)

(73) Assignee: Abbott Vascular Inc., Redwood City, CA (US)

( * ) Notice: Subject to any disclaimer, the term of this patent is extended or adjusted under 35 U.S.C. 154(b) by 377 days.

This patent is subject to a terminal disclaimer.

(21) Appl. No.: 11/113,549

(22) Filed: Apr. 25, 2005

(65) Prior Publication Data

US 2005/0216057 A1 Sep. 29, 2005

Related U.S. Application Data

(63) Continuation of application No. 10/455,768, filed on Jun. 4, 2003, now Pat. No. 6,926,731, which is a continuation of application No. 09/948,813, filed on Sep. 7, 2001, now Pat. No. 6,582,452.

(30) Foreign Application Priority Data

Sep. 8, 2000 (IE) .................................. S2000/0722
Sep. 8, 2000 (IE) .................................. S2000/0724

(51) Int. Cl.
*A61B 17/08* (2006.01)

(52) U.S. Cl.
USPC .... 606/213; 606/142; 604/168.01; 227/175.1

(58) Field of Classification Search
USPC .......................... 606/213, 142, 139–140, 216; 227/175.1; 604/168.01
See application file for complete search history.

(56) References Cited

U.S. PATENT DOCUMENTS 287,046 A 10/1883 Norton
438,400 A 10/1890 Brennen
(Continued)

FOREIGN PATENT DOCUMENTS

AU 2003297432 12/2003
CA 2 339 060 2/2000
(Continued)

OTHER PUBLICATIONS

U.S. Appl. No. 09/866,551, filed May 25, 2001.
(Continued)

*Primary Examiner* — Darwin Erezo
*Assistant Examiner* — Diane Yabut
(74) *Attorney, Agent, or Firm* — Workman Nydegger; Randy Shen

(57) ABSTRACT

A surgical stapler having a hollow shaft 10 and a tube 92 slidable axially within the shaft between a forward position wherein one end 96 of the tube projects beyond a free end of the shaft to enter a puncture site in a blood vessel and a rearward position wherein the end of the locator tube is retracted within the shaft. A surgical staple 40 straddles the tube 92 and is slidable thereon forwardly towards an anvil 24 against which the staple may be deformed to staple together the opposite edges of the puncture site. A cam mechanism drives the staple forwardly along the tube 92 into deforming engagement with the anvil and at the same time retracts the tube into the shaft in time to allow the legs of the staple to close onto the puncture site.

22 Claims, 19 Drawing Sheets

(56) References Cited

U.S. PATENT DOCUMENTS

| | | |
|---|---|---|
| 556,082 A | 3/1896 | Boeddinghaus |
| 1,088,393 A | 2/1914 | Backus |
| 1,242,139 A | 10/1917 | Callahan |
| 1,331,401 A | 2/1920 | Summers |
| 1,426,111 A | 8/1922 | Sacker |
| 1,480,935 A | 1/1924 | Gleason |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,682,180 A | 8/1972 | McFarlane |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,960,147 A | 6/1976 | Murray |
| 3,976,079 A | 8/1976 | Samuels et al. |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,595,559 A | 6/1986 | Fleischhacker |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae |
| 4,836,204 A | 6/1989 | Landymore |
| 4,852,568 A | 8/1989 | Kensey |
| 4,860,746 A | 8/1989 | Yoon |

(56) References Cited

U.S. PATENT DOCUMENTS

| | | |
|---|---|---|
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl |
| 5,156,609 A | 10/1992 | Nakao et al. |
| 5,158,566 A | 10/1992 | Pianetti |
| 5,160,339 A | 11/1992 | Chen et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,682 A | 1/1993 | Chow |
| 5,176,691 A | 1/1993 | Pierce |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,203,787 A | 4/1993 | Noblitt et al. |
| 5,209,756 A | 5/1993 | Seedhorm et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman |
| 5,242,456 A | 9/1993 | Nash et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel |
| 5,292,332 A | 3/1994 | Lee |
| 5,304,183 A | 4/1994 | Gourlay et al. |
| 5,304,184 A | 4/1994 | Hathaway |
| 5,304,204 A | 4/1994 | Bregen |
| 5,306,254 A * | 4/1994 | Nash et al. ............... 604/168.01 |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez et al. |
| 5,395,030 A | 3/1995 | Kuramoto |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |
| 5,411,520 A | 5/1995 | Nash et al. |
| 5,413,571 A | 5/1995 | Katsaros |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |

(56) References Cited

U.S. PATENT DOCUMENTS

| | | |
|---|---|---|
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,558 A | 10/1995 | Kolesa et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss |
| 5,471,982 A | 12/1995 | Edwards et al. |
| 5,474,557 A | 12/1995 | Mai |
| 5,474,569 A | 12/1995 | Zinreich et al. |
| 5,474,572 A | 12/1995 | Hayhurst |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,492,119 A | 2/1996 | Abrams |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. |
| 5,514,159 A | 5/1996 | Matula et al. |
| 5,521,184 A | 5/1996 | Zimmerman |
| 5,522,840 A | 6/1996 | Krajicek |
| 5,527,322 A | 6/1996 | Klein |
| 5,536,251 A | 7/1996 | Evard |
| 5,536,267 A | 7/1996 | Edwards |
| 5,540,712 A | 7/1996 | Kleshinski et al. |
| 5,540,716 A | 7/1996 | Hlavacek |
| 5,543,520 A | 8/1996 | Zimmerman |
| 5,544,802 A | 8/1996 | Crainich |
| 5,547,474 A | 8/1996 | Kloeckl et al. |
| 5,560,532 A | 10/1996 | Defonzo |
| 5,562,684 A | 10/1996 | Kammerer |
| 5,571,120 A | 11/1996 | Yoon |
| 5,573,540 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,593,422 A | 1/1997 | Muijs Van der Moer et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,613,975 A | 3/1997 | Christy |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs Van De Moer |
| 5,626,614 A | 5/1997 | Hart |
| 5,630,824 A | 5/1997 | Hart |
| 5,634,936 A | 6/1997 | Lindon et al. |
| 5,643,318 A | 7/1997 | Tsukernik |
| 5,645,553 A | 7/1997 | Kolesa et al. |
| 5,645,565 A | 7/1997 | Rudd et al. |
| 5,645,566 A | 7/1997 | Brenneman |
| 5,645,567 A | 7/1997 | Crainich |
| 5,647,372 A | 7/1997 | Tovey et al. |
| 5,649,959 A | 7/1997 | Hannam et al. |
| D383,539 S | 9/1997 | Croley |
| 5,669,917 A | 9/1997 | Sauer et al. |
| 5,669,935 A | 9/1997 | Rosenman et al. |
| 5,672,174 A | 9/1997 | Gough et al. |
| 5,674,231 A * | 10/1997 | Green et al. .......... 606/142 |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford |
| 5,695,505 A | 12/1997 | Yoon |
| 5,695,524 A | 12/1997 | Kelley et al. |
| 5,700,273 A | 12/1997 | Buelna et al. |
| 5,709,224 A | 1/1998 | Behl et al. |
| 5,709,708 A | 1/1998 | Thal |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,728,143 A | 3/1998 | Gough et al. |
| 5,732,872 A | 3/1998 | Bolduc et al. |
| 5,735,736 A | 4/1998 | Volk |
| 5,735,873 A | 4/1998 | MacLean |
| 5,735,875 A | 4/1998 | Bonutti et al. |
| 5,735,877 A | 4/1998 | Pagedas |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,759,189 A | 6/1998 | Ferragamo et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,147 A | 7/1998 | Dolendo |
| 5,776,150 A | 7/1998 | Nolan et al. |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |

(56) References Cited

U.S. PATENT DOCUMENTS

| | | |
|---|---|---|
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,159 A | 11/1999 | Bolduc et al. |
| 5,976,161 A | 11/1999 | Kirsch et al. |
| 5,976,174 A | 11/1999 | Ruiz |
| 5,980,517 A | 11/1999 | Gough |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu |
| 6,007,563 A * | 12/1999 | Nash et al. .................. 606/213 |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,071,300 A | 6/2000 | Brenneman et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo et al. |
| 6,117,157 A | 9/2000 | Tekulve |
| 6,117,159 A | 9/2000 | Huebsch et al. |
| 6,120,513 A | 9/2000 | Bailey et al. |
| 6,120,524 A | 9/2000 | Taheri |
| 6,126,675 A | 10/2000 | Schervinsky et al. |
| 6,126,677 A | 10/2000 | Ganaja et al. |
| 6,136,010 A | 10/2000 | Modesitt et al. |
| 6,143,004 A | 11/2000 | Davis |
| 6,143,017 A | 11/2000 | Thal |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,174,324 B1 | 1/2001 | Egan et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,231,592 B1 | 5/2001 | Bonutti et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,870 B1 | 10/2001 | Jacobsen et al. |
| 6,302,898 B1 | 10/2001 | Edwards et al. |

(56) References Cited

U.S. PATENT DOCUMENTS

| | | |
|---|---|---|
| 6,305,891 B1 | 10/2001 | Burlingame |
| 6,306,081 B1 | 10/2001 | Ishikawa et al. |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,498 B1 | 2/2003 | Burbank et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,645,255 B2 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,051 B2 | 2/2004 | Nakada et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 * | 8/2005 | Coleman et al. ............... 606/213 |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |

(56) References Cited

U.S. PATENT DOCUMENTS

| | | |
|---|---|---|
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,261,716 B2 | 8/2007 | Strobel et al. |
| 7,270,672 B1 | 9/2007 | Singer |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada |
| 2002/0022822 A1 | 2/2002 | Cragg et al. |
| 2002/0026208 A1 | 2/2002 | Belef |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049472 A1 | 4/2002 | Coleman et al. |
| 2002/0058960 A1 | 5/2002 | Hudson et al. |
| 2002/0062104 A1 | 5/2002 | Ashby et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188275 A1 | 12/2002 | McGuckin et al. |
| 2002/0193808 A1 | 12/2002 | Belef et al. |
| 2002/0198562 A1 | 12/2002 | Ackerfeldt et al. |
| 2002/0198589 A1 | 12/2002 | Leong |
| 2003/0004543 A1* | 1/2003 | Gleeson et al. ............... 606/213 |
| 2003/0009180 A1 | 1/2003 | Hinchliffe et al. |
| 2003/0009196 A1 | 1/2003 | Peterson |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |

(56) References Cited

U.S. PATENT DOCUMENTS

| | | |
|---|---|---|
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0287967 A1 | 11/2008 | Andreas et al. |
| 2008/0287988 A1 | 11/2008 | Smith et al. |
| 2008/0300628 A1 | 12/2008 | Ellingwood |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0060355 A1 | 3/2011 | Carley et al. |
| 2011/0066163 A1 | 3/2011 | Cho et al. |
| 2011/0066164 A1 | 3/2011 | Walberg et al. |
| 2011/0071565 A1 | 3/2011 | Ginn |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Karineimi et al. |
| 2012/0245626 A1 | 9/2012 | Ellingwood et al. |
| 2012/0310261 A1 | 12/2012 | Cummins |
| 2013/0006274 A1 | 1/2013 | Walberg et al. |
| 2013/0338708 A1 | 12/2013 | Cummins et al. |

FOREIGN PATENT DOCUMENTS

| | | |
|---|---|---|
| DE | 197 11 288 | 1/1998 |
| DE | 297 23 736 U 1 | 4/1999 |
| DE | 19859952 | 2/2000 |

(56) References Cited

FOREIGN PATENT DOCUMENTS

| | | |
|---|---|---|
| DE | 102006056283 | 6/2008 |
| EP | 0 386 361 | 9/1990 |
| EP | 0534696 | 3/1993 |
| EP | 0 621 032 | 10/1994 |
| EP | 0 756 851 | 2/1997 |
| EP | 0 744 237 | 5/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2443238 | 7/1980 |
| FR | 2 715 290 | 7/1995 |
| FR | 2 722 975 | 2/1996 |
| FR | 2 768 324 | 3/1999 |
| GB | 2 075 144 | 11/1981 |
| GB | 2 397 240 | 7/2004 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0452 | 12/2002 |
| IE | S 2002/0664 | 2/2003 |
| IE | S 2002/0665 | 2/2003 |
| IE | S 2002/0451 | 7/2003 |
| IE | S 2002/0552 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| IO | 1358466 | 7/1974 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO-97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO-98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO-0007640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, Aug. 27, 2004.
2002/0072768, Office Action, Feb. 23, 2005.
2002/0072768, Office Action, Apr. 11, 2005.
2002/0072768, Office Action, Jul. 27, 2005.
2002/0072768, Office Action, Mar. 6, 2006.
2002/0072768, Office Action, May 24, 2006.
2002/0072768, Office Action, Oct. 26, 2006.

(56) References Cited

OTHER PUBLICATIONS

2002/0072768, Office Action, Apr. 19, 2007.
2002/0133193, Office Action, Nov. 4, 2004.
2002/0133193, Office Action, May 4, 2005.
2002/0133193, Office Action, Oct. 18, 2005.
2002/0133193, Notice of Allowance, Apr. 18, 2007.
2002/0133193, Notice of Allowance, Sep. 27, 2007.
2003/0078598, Office Action, Feb. 9, 2005.
2003/0078598, Office Action, May 26, 2005.
2003/0078598, Office Action, Oct. 4, 2005.
2003/0078598, Notice of Allowance, May 10, 2006.
2003/0078598, Notice of Allowance, Jul. 2, 2007.
2003/0195561, Office Action, Jun. 10, 2004.
2003/0195561, Notice of Allowance, Sep. 21, 2004.
2003/0195561, Office Action, Jan. 3, 2006.
2003/0195561, Issue Notification, Feb. 15, 2006.
2003/0195561, Office Action, May 16, 2006.
2003/0195561, Notice of Allowance, Dec. 28, 2006.
2003/0195561, Notice of Allowance, Jul. 10, 2007.
2003/0195561, Notice of Allowance, Aug. 2, 2007.
2004/0153123, Office Action, Sep. 22, 2006.
2004/0153123, Office Action, Jan. 31, 2007.
2004/0153123, Office Action, Sep. 18, 2007.
2004/0153122, Office Action, Nov. 30, 2005.
2004/0153122, Office Action, Aug. 23, 2006.
2004/0153122, Office Action, Feb. 13, 2007.
2004/0153122, Office Action, Sep. 12, 2007.
2004/0073255, Office Action, Sep. 15, 2006.
2004/0073255, Office Action, Apr. 18, 2007.
2004/0073236, Office Action, Sep. 19, 2006.
2004/0073236, Office Action, May 2, 2007.
2004/0009289, Office Action, Jun. 30, 2006.
2004/0009289, Office Action, Oct. 20, 2006.
2004/0009289, Office Action, May 29, 2007.
2004/0167570, Office Action, Oct. 30, 2006.
2004/0167570, Office Action, Apr. 17, 2007.
2004/0167570, Office Action, Aug. 31, 2007.
2005/0274768, Office Action, Oct. 19, 2006.
2005/0274768, Office Action, Aug. 10, 2007.
2005/0234508, Office Action, Aug. 13, 2007.
2006/0135989, Office Action, Nov. 30, 2006.
2006/0135989, Office Action, Sep. 5, 2007.
2006/0195124, Office Action, Jun. 6, 2007.
2006/0195123, Office Action, May 14, 2007.
6,197,042, Notice of Allowance, Nov. 6, 2000.
6,197,042, Issue Notification, Feb. 15, 2001.
6,277,140, Office Action, Mar. 26, 2001.
6,277,140, Notice of Allowance, Jun. 4, 2001.
6,277,140, Issue Notification, Aug. 6, 2001.
6,391,048, Notice of Allowance, Mar. 26, 2001.
6,391,048, Office Action, Sep. 5, 2001.
6,391,048, Notice of Allowance, Feb. 11, 2002.
6,391,048, Issue Notification, May 3, 2002.
6,461,364, Notice of Allowance, May 6, 2002.
6,461,364, Issue Notification, Sep. 19, 2002.
6,582,452, Notice of Allowance, Jan. 31, 2003.
6,582,452, Issue Notification, Jun. 5, 2003.
6,616,686, Office Action, Dec. 17, 2002.
6,616,686, Notice of Allowance, Apr. 21, 2003.
6,616,686, Issue Notification, Aug. 21, 2003.
6,623,510, Notice of Allowance, Apr. 11, 2003.
6,623,510, Office Action, Jun. 9, 2003.
6,623,510, Issue Notification, Sep. 4, 2003.
6,632,238, Office Action, Feb. 26, 2003.
6,632,238, Notice of Allowance, Jun. 16, 2003.
6,632,238, Issue Notification, Sep. 25, 2003.
6,669,714, Office Action, Mar. 4, 2003.
6,669,714, Notice of Allowance, Jul. 28, 2003.
6,669,714, Issue Notification, Dec. 11, 2003.
6,695,867, Notice of Allowance, Sep. 29, 2003.
6,695,867, Issue Notification, Feb. 5, 2004.
6,719,777, Office Action, Feb. 20, 1987.
6,719,777, Notice of Allowance, Jul. 24, 1987.
6,719,777, Issue Notification, Mar. 25, 2004.
6,749,621, Notice of Allowance, Feb. 9, 2004.
6,749,621, Office Action, Apr. 13, 2004.
6,749,621, Issue Notification, May 27, 2004.
6,780,197, Office Action, Sep. 11, 2003.
6,780,197, Office Action, Feb. 9, 2004.
6,780,197, Notice of Allowance, Mar. 17, 2004.
6,780,197, Issue Notification, Aug. 5, 2004.
6,926,731, Office Action, Nov. 16, 2004.
6,926,731, Notice of Allowance, Apr. 6, 2005.
6,926,731, Issue Notification, Jul. 20, 2005.
6,942,674, Office Action, Sep. 29, 2004.
6,942,674, Notice of Allowance, May 13, 2005.
6,942,674, Issue Notification, Aug. 24, 2005.
7,001,398, Office Action, Mar. 22, 2005.
7,001,398, Notice of Allowance, Jul. 6, 2005.
7,001,398, Notice of Allowance, Oct. 5, 2005.
7,001,398, Issue Notification, Feb. 21, 2006.
7,008,435, Office Action, Apr. 20, 2005.
7,008,435, Office Action, Aug. 10, 2005.
7,008,435, Notice of Allowance, Oct. 18, 2005.
7,008,435, Issue Notification, Feb. 15, 2006.
7,108,709, Office Action, Jul. 27, 2004.
7,108,709, Office Action, Dec. 17, 2004.
7,108,709, Notice of Allowance, Mar. 9, 2005.
7,108,709, Office Action, Aug. 11, 2006.
7,108,709, Issue Notification, Aug. 30, 2006.
7,111,768, Office Action, Feb. 23, 2006.
7,111,768, Notice of Allowance, May 31, 2006.
7,111,768, Issue Notification, Sep. 6, 2006.
7,163,551, Office Action, Jan. 10, 2006.
7,163,551, Notice of Allowance, Sep. 20, 2006.
7,163,551, Issue Notification, Dec. 27, 2006.
7,211,101, Office Action, Aug. 10, 2005.
7,211,101, Office Action, Dec. 19, 2005.
7,211,101, Office Action, Apr. 21, 2006.
7,211,101, Notice of Allowance, Dec. 27, 2006.
7,211,101, Issue Notification, Apr. 11, 2007.
"Hand tool for forming telephone connections—comprises pliers with reciprocably driven ram crimping clip around conductors against anvil", Derwent-ACC-No. 1978-B8090A.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 10/006,400, Apr. 2, 2008, Office Action.
U.S. Appl. No. 10/147,774, Feb. 4, 2008, Notice Of Allowance.
U.S. Appl. No. 10/147,774, Jun. 30, 2008, Office Action.
U.S. Appl. No. 10/264,306, May 26, 2005, Office Action.
U.S. Appl. No. 10/264,306, Feb. 4, 2008, Notice Of Allowance.
U.S. Appl. No. 10/264,306, Jun. 27, 2008, Office Action.
U.S. Appl. No. 10/356,214, Mar. 6, 2008, Office Action.
U.S. Appl. No. 10/435,104, Apr. 4, 2008, Notice Of Allowance.
U.S. Appl. No. 10/517,004, Jan. 30, 2008, Office Action.
U.S. Appl. No. 10/541,083, May 5, 2008, Office Action.
U.S. Appl. No. 10/638,115, Feb. 7, 2008, Office Action.
U.S. Appl. No. 10/667,144, May 12, 2008, Office Action.
U.S. Appl. No. 10/682,459, Apr. 2, 2008, Office Action.
U.S. Appl. No. 10/786,444, Apr. 24, 2008, Office Action.
U.S. Appl. No. 10/787,073, Feb. 22, 2008, Office Action.
U.S. Appl. No. 11/152,562, May 13, 2008, Office Action.
U.S. Appl. No. 11/344,891, Apr. 29, 2008, Office Action.
U.S. Appl. No. 11/406,203, May 23, 2008, Notice Of Allowance.
U.S. Appl. No. 11/411,925, Feb. 5, 2008, Office Action.

(56) References Cited

OTHER PUBLICATIONS

Deepak Mital et al, Renal Transplantation Without Sutures Using The Vascular Clipping System For Renal Artery And Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials And Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma—Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular And Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25—No. 2, Supplement 1.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 10/435,104, Sep. 26, 2008, Notice Of Allowance.
U.S. Appl. No. 10/541,083, Sep. 19, 2008, Notice Of Allowance.
U.S. Appl. No. 10/616,832, Sep. 17, 2008, Office Action.
U.S. Appl. No. 11/198,811, Aug. 26, 2008, Office Action.
U.S. Appl. No. 11/406,203, Sep. 22, 2008, Notice Of Allowance.
U.S. Appl. No. 60/696,069, filed Jul. 1, 2005, Pantages et al.
U.S. Appl. No. 60/946,026, filed Jun. 25, 2007, Ellingwood.
U.S. Appl. No. 12/393,877, filed Feb. 26, 2009, Ellingwood et al.
U.S. Appl. No. 12/403,277, filed Mar. 12, 2009, Coleman et al.
McCarthy, et al., "Tension (Stay) Suture Bridge", J. of International College of Surgeons, 34(5), pp. 613-614 (Nov. 1960).
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 10/006,400, Jan. 2, 2009, Office Action.
U.S. Appl. No. 10/006,400, Jul. 9, 2009, Notice of Allowance.
U.S. Appl. No. 10/147,774, Mar. 18, 2009, Office Action.
U.S. Appl. No. 10/264,306, Feb. 26, 2009, Office Action.
U.S. Appl. No. 10/264,306, Aug. 13, 2009, Office Action.
U.S. Appl. No. 10/305,923, Nov. 1, 2004, Office Action.
U.S. Appl. No. 10/305,923, Mar. 3, 2005, Notice of Allowance.

(56) References Cited

OTHER PUBLICATIONS

U.S. Appl. No. 10/356,214, Nov. 4, 2008, Office Action.
U.S. Appl. No. 10/356,214, Apr. 29, 2009, Office Action.
U.S. Appl. No. 10/435,104, Nov. 14, 2007, Supplemental Notice of Allowance.
U.S. Appl. No. 10/435,104, Dec. 22, 2008, Supplemental Notice of Allowance.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Jun. 26, 2009, Notice of Allowance.
U.S. Appl. No. 10/541,083, Oct. 31, 2007, Office Action.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/616,832, Jul. 21, 2009, Office Action.
U.S. Appl. No. 10/638,115, Oct. 29, 2008, Office Action.
U.S. Appl. No. 10/638,115, May 7, 2009, Notice of Allowance.
U.S. Appl. No. 10/667,144, Mar. 24, 2009, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Dec. 4, 2008, Office Action.
U.S. Appl. No. 10/682,459, Jun. 10, 2009, Office Action.
U.S. Appl. No. 10/786,444, Oct. 17, 2008, Office Action.
U.S. Appl. No. 10/786,444, Jun. 18, 2009, Office Action.
U.S. Appl. No. 10/787,073, Nov. 12, 2008, Office Action.
U.S. Appl. No. 10/787,073, Aug. 13, 2009, Office Action.
U.S. Appl. No. 10/908,721, Nov. 25, 2008, Office Action.
U.S. Appl. No. 10/908,721, Jun. 23, 2009, Office Action.
U.S. Appl. No. 11/048,503, Mar. 13, 2009, Office Action.
U.S. Appl. No. 11/048,503, Jun. 26, 2009, Office Action.
U.S. Appl. No. 11/152,562, Feb. 13, 2009, Office Action.
U.S. Appl. No. 11/152,562, Jul. 6, 2009, Office Action.
U.S. Appl. No. 11/198,811, Sep. 22, 2009, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Dec. 8, 2008, Office Action.
U.S. Appl. No. 11/344,891, Feb. 26, 2009, Office Action.
U.S. Appl. No. 11/390,586, Jun. 24, 2009, Office Action.
U.S. Appl. No. 11/396,141, May 22, 2009, Restriction Requirement.
U.S. Appl. No. 11/396,141, Aug. 26, 2009, Office Action.
U.S. Appl. No. 11/396,731, Feb. 13, 2009, Office Action.
U.S. Appl. No. 11/396,731, May 22, 2009, Office Action.
U.S. Appl. No. 11/406,203, Mar. 3, 2009, Office Action.
U.S. Appl. No. 11/406,203, Sep. 16, 2009, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/461,323, May 2, 2007, Office Action.
U.S. Appl. No. 11/461,323, Oct. 29, 2007, Office Action.
U.S. Appl. No. 11/461,323, Apr. 25, 2008, Office Action.
U.S. Appl. No. 11/461,323, Nov. 6, 2008, Office Action.
U.S. Appl. No. 11/461,323, Jul. 27, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/744,089, Nov. 26, 2008, Office Action.
U.S. Appl. No. 11/744,089, Aug. 14, 2009, Office Action.
U.S. Appl. No. 11/958,295, Aug. 27, 2009, Office Action.
U.S. Appl. No. 12/106,928, Jan. 23, 2009, Office Action.
U.S. Appl. No. 12/106,937, Mar. 30, 2009, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
Database WPI; Section PQ, Week 200120; Derwent Publications Ltd., London GB; AN 2001-203165; XP002199926 & ZA 200 100 528 A (Anthony T), Feb. 28, 2001 abstract.
U.S. Appl. No. 60/693,531, filed Jun. 24, 2005, Carly.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/147,774, Oct. 26, 2009, Office Action.
U.S. Appl. No. 10/147,774, Jun. 8, 2010, Office Action.
U.S. Appl. No. 10/264,306, Jan. 27, 2010, Office Action.
U.S. Appl. No. 10/264,306, Jun. 15, 2010, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/616,832, Jan. 11, 2010, Notice of Allowance.
U.S. Appl. No. 10/616,832, May 12, 2010, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Jan. 14, 2010, Office Action.
U.S. Appl. No. 10/787,073, Feb. 17, 2010, Notice of Allowance.
U.S. Appl. No. 10/908,721, Feb. 2, 2010, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/152,562, Mar. 31, 2010, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jul. 6, 2010, Office Action.
U.S. Appl. No. 11/396,141, May 4, 2010, Office Action.
U.S. Appl. No. 11/396,731, Jun. 29, 2010, Office Action.
U.S. Appl. No. 11/406,203, Jun. 18, 2010, Notice of Allowance.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.

(56) References Cited

OTHER PUBLICATIONS

U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Oct. 5, 2009, Office Action.
U.S. Appl. No. 12/106,928, May 10, 2010, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,277, Jul. 8, 2010, Office Action.
U.S. Appl. No. 29/296,370, Feb. 10, 2010, Issue Notification.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/541,083, Aug. 17, 2010, Notice of Allowance.
U.S. Appl. No. 10/638,115, Aug. 13, 2010, Notice of Allowance.
U.S. Appl. No. 10/787,073, Aug. 25, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/675,462, Aug. 31, 2010, Office Action.
U.S. Appl. No. 11/757,108, Nov. 25, 2009, Office Action.
U.S. Appl. No. 12/403,256, Aug. 19, 2010, Notice of Allowance.
U.S. Appl. No. 11/508,656, Aug. 30, 2010, Office Action.
U.S. Appl. No. 11/958,281, Sep. 2, 2010, Office Action.
U.S. Appl. No. 11/152,562, Sep. 16, 2010, Notice of Allowance.
U.S. Appl. No. 10/616,832, Sep. 20, 2010, Notice of Allowance.
U.S. Appl. No. 10/787,073, Sep. 15, 2010, Issue Notification.
U.S. Appl. No. 11/427,297, Sep. 15, 2010, Office Action.
U.S. Appl. No. 11/767,818, Sep. 30, 2010, Office Action.
U.S. Appl. No. 12/365,397, Sep. 13, 2010, Office Action.
U.S. Appl. No. 10/435,104, Oct. 5, 2010, Notice of Allowance.
U.S. Appl. No. 10/264,306, Oct. 29, 2010, Notice of Allowance.
U.S. Appl. No. 10/356,214, Sep. 3, 2010, Notice of Allowance.
U.S. Appl. No. 10/682,459, Oct. 12, 2010, Office Action.
U.S. Appl. No. 11/406,203, Oct. 6, 2010, Issue Notification.
U.S. Appl. No. 11/508,715, Oct. 18, 2010, Office Action.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 11/198,811, Oct. 20, 2010, Issue Notification.
U.S. Appl. No. 11/508,662, Oct. 26, 2010, Office Action.
U.S. Appl. No. 11/852,190, Nov. 1, 2010, Office Action.
U.S. Appl. No. 12/106,928, Oct. 25, 2010, Office Action.
U.S. Appl. No. 12/114,091, Oct. 27, 2010, Office Action.
U.S. Appl. No. 12/897,358, filed Oct. 4, 2010, Carley.
U.S. Appl. No. 12/961,331, filed Dec. 6, 2010, Voss.
U.S. Appl. No. 12/966,923, filed Dec. 13, 2010, Cummins et al.
U.S. Appl. No. 10/147,774, Dec. 2, 2010, Notice of Allowance.
U.S. Appl. No. 10/517,004, Nov. 23, 2010, Issue Notification.
U.S. Appl. No. 10/541,083, Dec. 1, 2010, Issue Notification.
U.S. Appl. No. 11/048,503, Dec. 8, 2010, Issue Notification.
U.S. Appl. No. 11/427,309, Nov. 15, 2010, Office Action.
U.S. Appl. No. 11/959,334, Nov. 10, 2010, Issue Notification.
U.S. Appl. No. 12/114,031, Nov. 22, 2010, Office Action.
U.S. Appl. No. 12/403,256, Nov. 23, 2010, Issue Notification.
U.S. Appl. No. 12/113,851, Dec. 16, 2010, Office Action.
U.S. Appl. No. 12/114,091, Dec. 17, 2010, Office Action.
U.S. Appl. No. 13/112,631, Jun. 26, 2013, Office Action.
U.S. Appl. No. 12/114,091, Jul. 7, 2011, Office Action.
U.S. Appl. No. 12/945,646, Jul. 6, 2011, Office Action.
U.S. Appl. No. 12/608,773, Jan. 7, 2013, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 12/338,977, Jan. 19, 2012, Office Action.
U.S. Appl. No. 12/684,569, Jan. 27, 2012, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/961,331, Feb. 1, 2013, Office Action.
U.S. Appl. No. 13/488,233, Feb. 5, 2013, Notice of Allowance.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 11/396,141, Nov. 4, 2013, Notice of Allowance.
U.S. Appl. No. 11/411,925, Oct. 1, 2013, Office Action.
U.S. Appl. No. 11/411,925, Feb. 5, 2014, Notice of Allowance.
U.S. Appl. No. 11/455,993, Jan. 29, 2014, Office Action.
U.S. Appl. No. 11/532,325, Dec. 2, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 12/106,928, Dec. 2, 2013, Office Action.
U.S. Appl. No. 12/106,937, Jan. 22, 2014, Office Action.
U.S. Appl. No. 12/122,603, Nov. 20, 2013, Office Action.
U.S. Appl. No. 12/403,277, Jan. 27, 2014, Office Action.
U.S. Appl. No. 12/642,319, Dec. 16, 2013, Office Action.
U.S. Appl. No. 12/688,065, Oct. 18, 2013, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014, Notice of Allowance.
U.S. Appl. No. 12/961,331, Sep. 20, 2013, Advisory Action.
U.S. Appl. No. 12/987,792, Jan. 21, 2014, Office Action.
U.S. Appl. No. 13/030,922, Jan. 8, 2014, Notice of Allowance.
U.S. Appl. No. 13/052,634, Nov. 8, 2013, Office Action.
U.S. Appl. No. 13/112,618, Nov. 20, 2013, Office Action.
U.S. Appl. No. 13/112,631, Dec. 2, 2013, Office Action.
U.S. Appl. No. 13/153,594, Oct. 16, 2013, Notice of Allowance.
U.S. Appl. No. 13/153,594, Feb. 27, 2014, Issue Notification.
U.S. Appl. No. 13/791,829, Oct. 8, 2013, Notice of Allowance.
U.S. Appl. No. 13/898,202, Jan. 3, 2014, Office Action.
U.S. Appl. No. 13/222,899, Jan. 10, 2014, Office Action.
U.S. Appl. No. 12/402,398, Mar. 13, 2013, Notice of Allowance.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/114,091, Apr. 5, 2012, Office Action.
U.S. Appl. No. 12/684,542, Apr. 16, 2012, Office Action.
U.S. Appl. No. 12/941,809, filed Nov. 8, 2010, Ginn et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 13/030,922, filed Feb. 18, 2011, Cummins.

(56) References Cited

OTHER PUBLICATIONS

U.S. Appl. No. 13/039,087, filed Mar. 2, 2011, Palermo et al.
U.S. Appl. No. 10/147,774, Apr. 6, 2011, Issue Notification.
U.S. Appl. No. 10/638,115, Dec. 22, 2010, Issue Notification.
U.S. Appl. No. 10/682,459, Apr. 1, 2011, Notice of Allowance.
U.S. Appl. No. 11/396,731, Mar. 22, 2011, Office Action.
U.S. Appl. No. 11/427,297, Mar. 21, 2011, Office Action.
U.S. Appl. No. 11/767,818, Feb. 16, 2011, Office Action.
U.S. Appl. No. 11/852,190, Mar. 2, 2011, Office Action.
U.S. Appl. No. 11/958,281, Mar. 10, 2011, Office Action.
U.S. Appl. No. 12/122,603, Mar. 3, 2011, Office Action.
U.S. Appl. No. 12/402,398, Jan. 24, 2011, Office Action.
U.S. Appl. No. 12/403,277, Mar. 31, 2011, Office Action.
U.S. Appl. No. 12/945,646, Jan. 20, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 12/113,851, Apr. 27, 2011, Office Action.
U.S. Appl. No. 12/114,031, May 11, 2011, Office Action.
U.S. Appl. No. 12/122,603, Apr. 22, 2011, Office Action.
U.S. Appl. No. 12/143,020, May 11, 2011, Office Action.
U.S. Appl. No. 12/481,377, Apr. 28, 2011, Office Action.
U.S. Appl. No. 12/955,859, May 26, 2011, Office Action.
U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 12/608,773, Jun. 7, 2012, Office Action.
U.S. Appl. No. 13/026,989, Jun. 8, 2012, Office Action.
U.S. Appl. No. 12/338,977, Jun. 19, 2013, Office Action.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 11/675,462, Dec. 22, 2011, Notice of Allowance.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 12/135,858, Jul. 13, 2011, Office Action.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Aug. 3, 2011, Office Action.
U.S. Appl. No. 12/114,031, Aug. 2, 2011, Office Action.
U.S. Appl. No. 11/396,141, Aug. 21, 2013, Office Action.
U.S. Appl. No. 13/490,143, Aug. 21, 2013, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 12/897,358, Jan. 12, 2012, Notice of Allowance.
U.S. Appl. No. 12/113,851, Mar. 29, 2012, Office Action.
U.S. Appl. No. 12/403,277, Apr. 3, 2012, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 13/308,227, filed Nov. 30, 2011, Yibarren.
U.S. Appl. No. 12/688,065, Apr. 26, 2012, Office Action.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 13/153,594, filed Jun. 6, 2011, Reyes et al.
U.S. Appl. No. 10/667,144, Jun. 6, 2011, Office Action.
U.S. Appl. No. 12/481,377, Jun. 21, 2011, Office Action.
U.S. Appl. No. 11/344,891, Jun. 26, 2013, Issue Notification.
U.S. Appl. No. 12/106,928, Jun. 28, 2013, Office Action.
U.S. Appl. No. 12/106,937, Jun. 28, 2013, Office Action.
U.S. Appl. No. 12/402,398, Jun. 26, 2013, Issue Notification.
U.S. Appl. No. 12/941,809, Jul. 3, 2013, Office Action.
U.S. Appl. No. 12/961,331, Jul. 3, 2013, Office Action.
U.S. Appl. No. 10/786,444, Jul. 11, 2013, Notice of Allowance.
U.S. Appl. No. 13/615,547, Jul. 10, 2013, Issue Notification.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 12/955,859, Jul. 21, 2011, Office Action.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 10/682,459, Aug. 10, 2011, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 13/026,989, Aug. 23, 2013, Office Action.
U.S. Appl. No. 13/308,227, Sep. 11, 2013, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 13/026,989, Sep. 16, 2011, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 12/987,792, Sep. 17, 2012, Office Action.

(56) References Cited

OTHER PUBLICATIONS

U.S. Appl. No. 10/667,144, Oct. 28, 2011, Notice of Allowance.
U.S. Appl. No. 12/945,646, Oct. 26, 2011, Office Action.
2006/0144479, Office Action, Oct. 16, 2007.
Stretch Comb by Scunci, retrieved via internet at www.scunci.com/productdetail by examiner on Oct. 9, 2007, publication date unavailable.

* cited by examiner

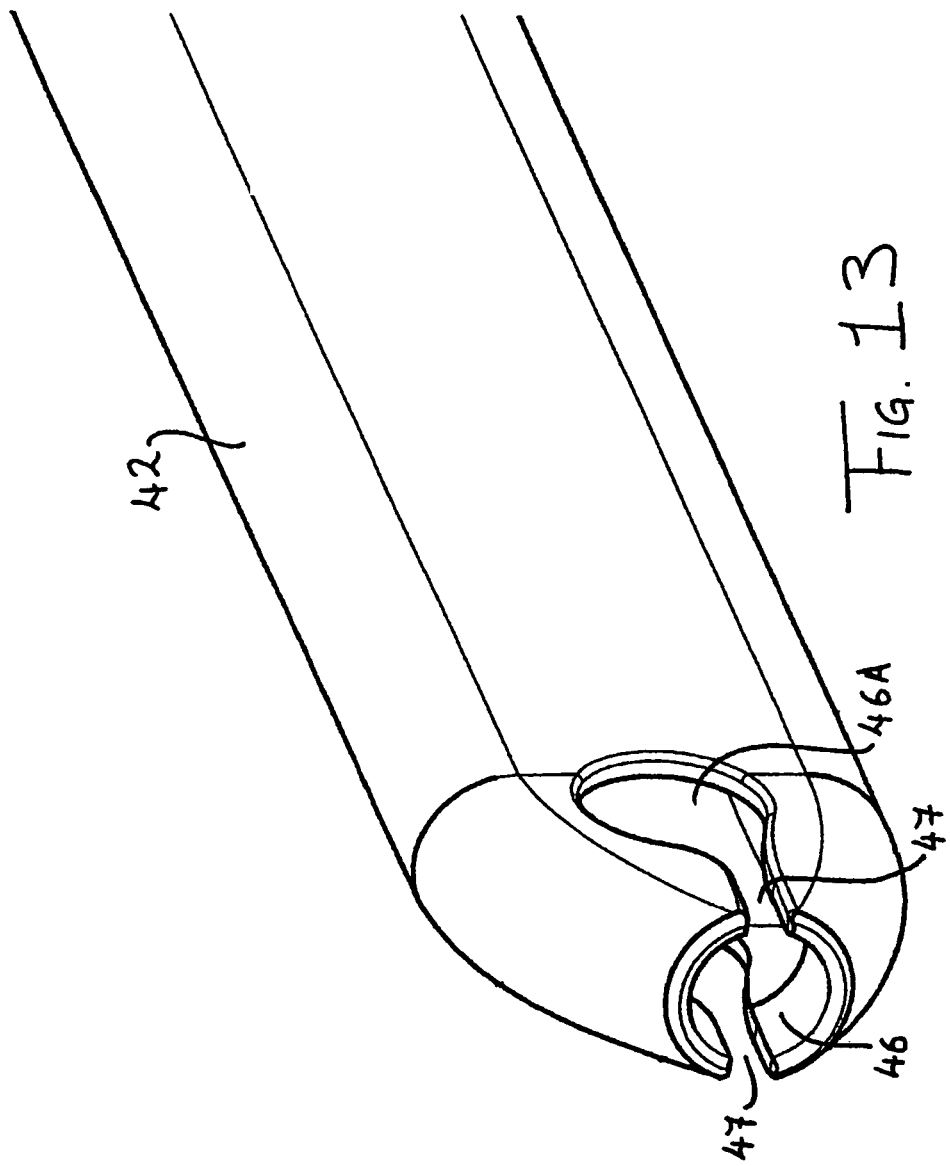

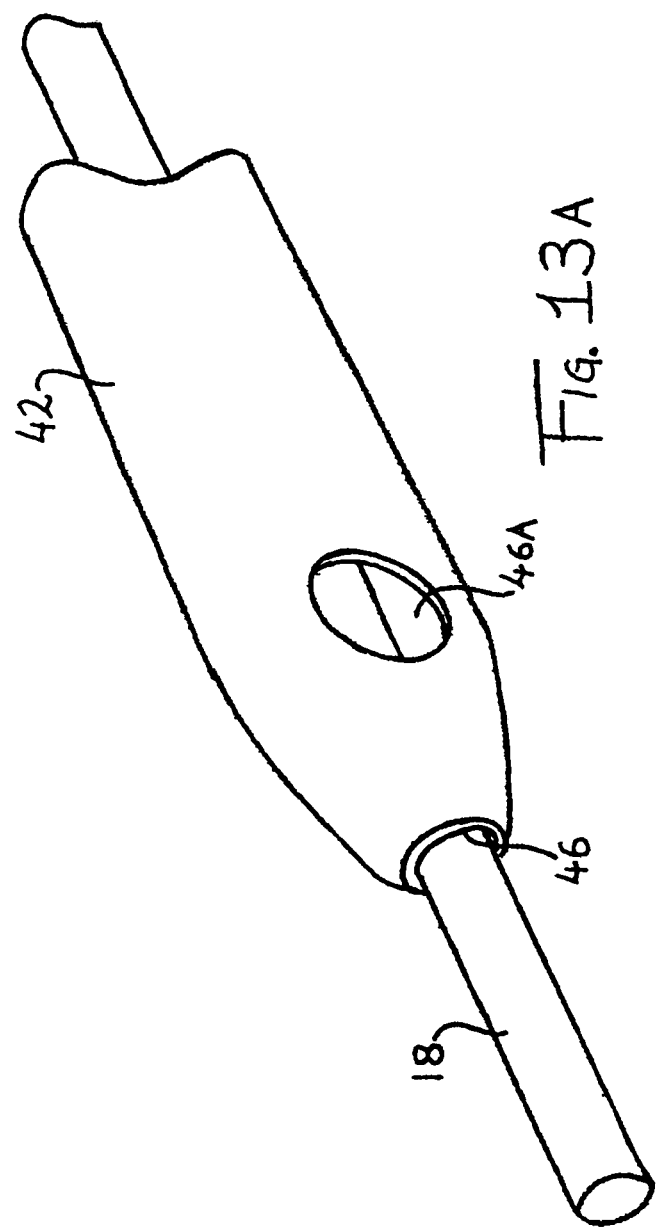

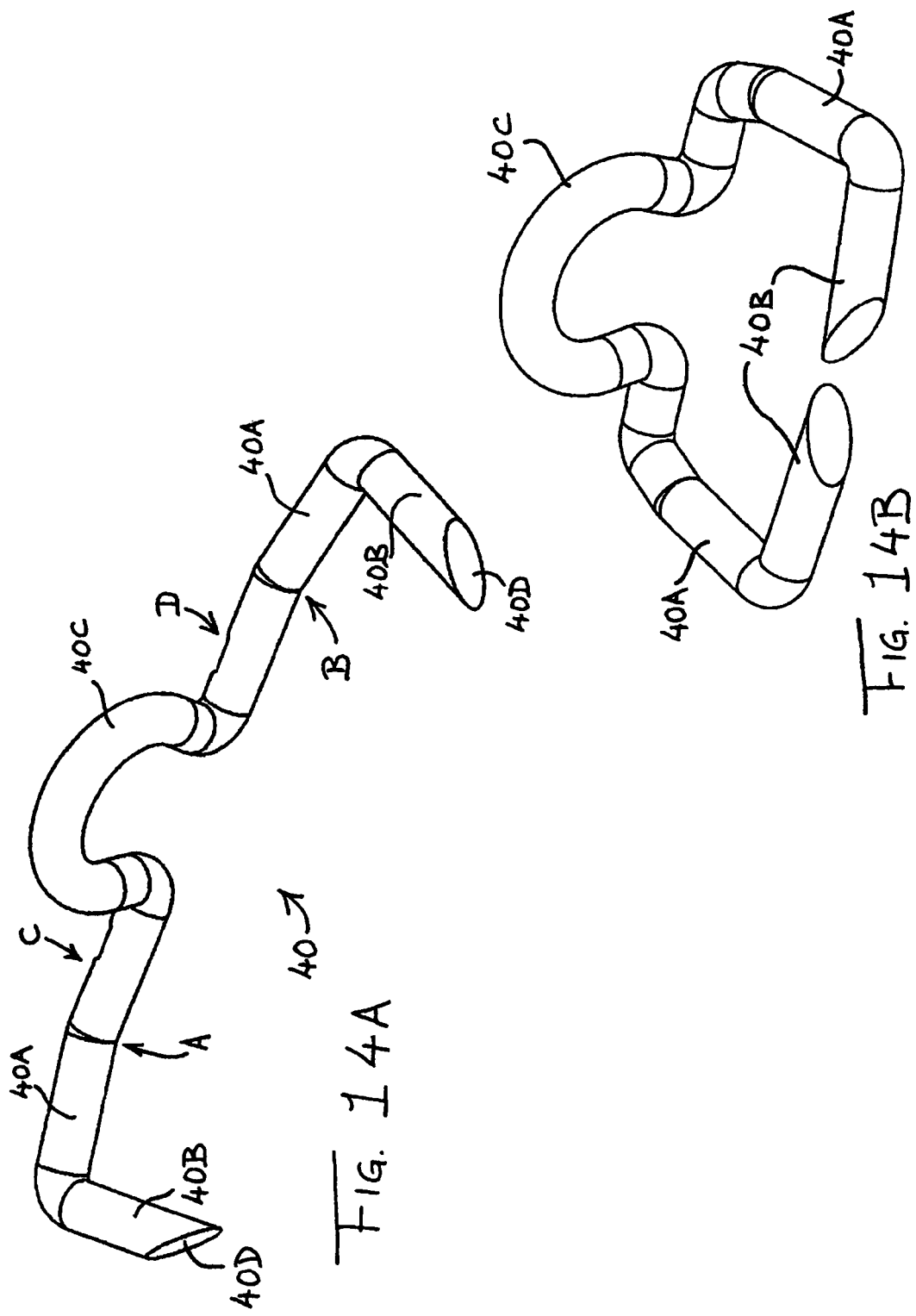

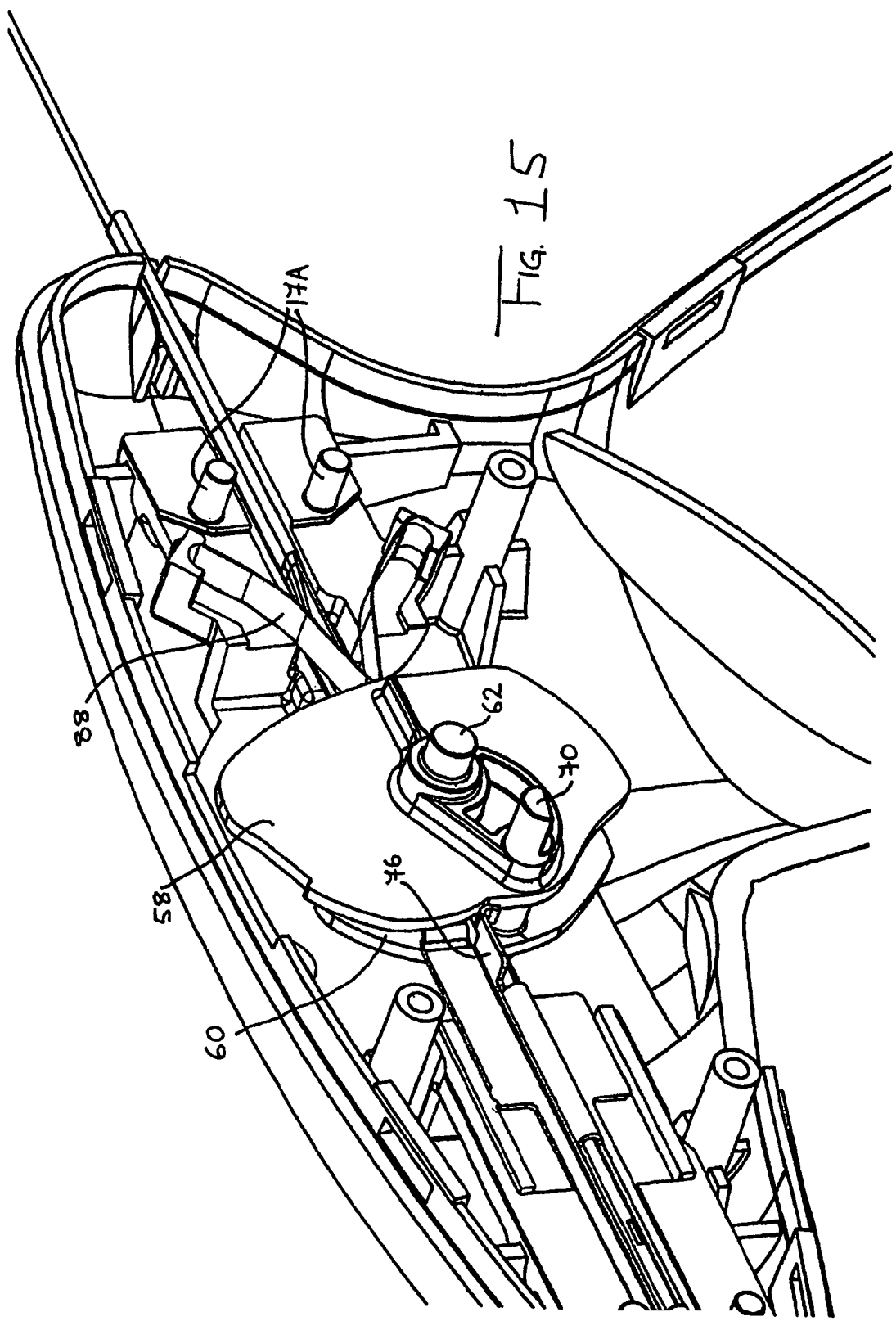

SURGICAL STAPLER

CROSS-REFERENCE TO RELATED APPLICATIONS

This application is a continuation of application Ser. No. 10/455,768 filed Jun. 4, 2003, now U.S. Pat. No. 6,926,731, which is a continuation of application Ser. No. 09/948,813, filed Sep. 7, 2001, now U.S. Pat. No. 6,582,452, entitled "Surgical Stapler," which claims priority to Ireland Application No. S2000/0722, filed Sep. 8, 2000 and Ireland Application No. S2000/0724, filed Sep. 8, 2000, each of which are hereby incorporated by reference in their entirety.

FIELD OF THE INVENTION

The present invention relates to an instrument, herein called a surgical stapler, for closing a puncture in a liquid-carrying vessel by applying a staple across the puncture so as to effect a closure. The invention relates particularly to surgical staplers for closing punctures in blood vessels.

BACKGROUND TO THE INVENTION

When performing catheterisation procedures, such as angiography or angioplasty, a catheter is generally introduced into the vascular system by first penetrating the skin, underlying tissues and blood vessel with a sharpened hollow needle. Next, a guidewire is commonly inserted through the lumen of the hollow needle and is caused to enter the selected blood vessel. Subsequently the needle is typically stripped off the guidewire and a combination of a dilator and/or introducer (or an introducer alone) are fed over the guidewire and pushed through the skin to enter the blood vessel. The guidewire can then be removed and a desired catheter to carry out the procedure is fed through the lumen of the introducer and advanced through the vascular system until the working end of the catheter is appropriately positioned. Following the conclusion of the catheterisation procedure the working catheter will be withdrawn and subsequently the dilator and/or introducer will also be removed from the wound. Following this procedure the vessel puncture must be closed in order to prevent loss of blood through the puncture hole.

Typically the wound is closed by maintaining external pressure over the vessel until the puncture naturally seals. This procedure can take approximately 30 minutes with the length of time usually being greater if the patient is hypertensive or anticoagulated. The procedure can also be uncomfortable for the patient and involves costly professional time on the part of the hospital staff. Other pressure techniques such as pressure bandages, sandbags or clamps have been employed but these also involve ensuring the patient remains motionless for an extended period of time and is monitored to ensure the effectiveness of the procedure.

A number of devices have been developed in recent times which provide an obstruction in the area of the puncture in order to prevent bleeding. For example, U.S. Pat. Nos. 4,852,568 and 4,890,612 disclose a device which utilises a collagen plug which when placed at the blood vessel opening absorbs body fluids, swells and affects a seal. Other plug like devices, for example U.S. Pat. Nos. 5,222,974 and 5,282,827, describe a plug and anchor device, the anchor being positioned inside the vessel and the collagen plug outside the vessel thereby sandwiching the puncture between both and effecting a closure.

WO 98/17179 discloses a surgical stapler having a blood locator tube adjacent the stapling head. A guidewire passes through an opening at the end of the tube and up through a hollow bore in the tube, so that the stapler can be fed onto the guidewire and down onto the puncture site. When the device reaches the puncture site, the tip of the tube enters the blood flow within the artery and blood passes through the tube and out of the distal end at a point visible to the clinician. The clinician can then actuate the stapling mechanism in the knowledge that the stapling head is at the puncture site in the arterial wall.

It is an object of the present invention to provide an instrument for closing a puncture in a liquid-carrying vessel by stapling.

SUMMARY OF THE INVENTION

According to one exemplary embodiment of the present invention, a surgical stapler is provided having a shaft, a locator slidable axially of the shaft between a forward position wherein the locator projects beyond a free end of the shaft to enter a puncture site in a liquid-carrying vessel in a human or animal, thereby to locate the free end of the shaft at the puncture site, and a rearward position wherein the locator is retracted relative to the shaft, a surgical staple straddling the locator and slidable forwardly thereon, said staple having forwardly pointing legs disposed respectively on opposite sides of the locator, an anvil against which the staple may be deformed to staple together opposite edges of the puncture site, and an actuator for driving the staple forwardly along the locator into deforming engagement with the anvil and for retracting the locator in co-ordination with the movement of the staple such that the locator is withdrawn from between the legs of the staple in time to allow the legs of the staple to staple together opposite edges of the puncture site.

In another aspect the invention provides a method of stapling closed a puncture site in a liquid-carrying vessel in a human or animal body, comprising the steps of: introducing a stapling mechanism to the location of the vessel; positioning the stapling mechanism at the puncture site by means of a locator associated with the stapling mechanism and projecting forwardly thereof, the locator sensing the position of the puncture site by entering the vessel at the site; delivering a staple to, and deforming the staple to close, the puncture site; and in co-ordination with the delivery and deformation of the staple, withdrawing the locator from the puncture site such that the locator is fully withdrawn from the vessel by the time the staple is fully deformed to close the puncture site. Preferably, the steps of delivering and deforming the staple and in co-ordination therewith withdrawing the locator are effected by operating a single control on a stapler actuating mechanism.

BRIEF DESCRIPTION OF THE DRAWINGS

Exemplary embodiments of the invention will now be described, by way of example, with reference to the accompanying drawings, in which:

FIG. 1(A) is an enlarged perspective view of the free end of the shaft of the stapler of FIG. 1;

FIG. 13 is a perspective view of the front portion of the blood locator tube shown in FIG. 12;

FIG. 13(A) is a perspective view of the front portion of an alternative embodiment of the blood locator tube shown in FIG. 12;

FIG. 14(A) is a perspective view of the surgical staple in the pre-fire (pre-deformed) state;

FIG. 14(B) is a perspective view of the surgical staple in the post-fire (deformed) state;

FIG. 15 is an enlarged perspective view of the cam mechanism;

DETAILED DESCRIPTION OF THE PREFERRED EMBODIMENTS

Figure 2:
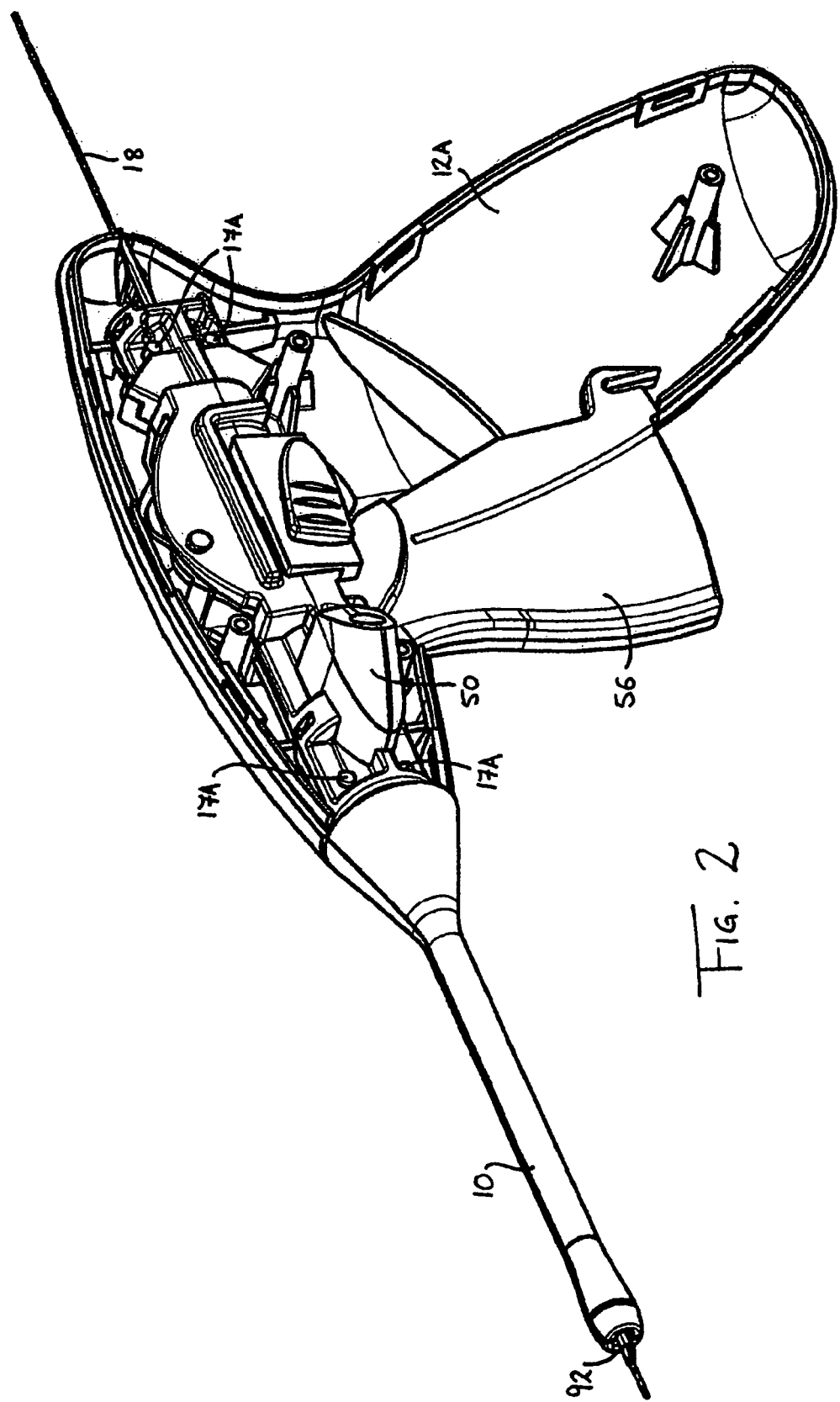
FIG. 2 is a perspective view of the stapler of FIG. 1 with the left-hand side handle removed.
Figure 4:
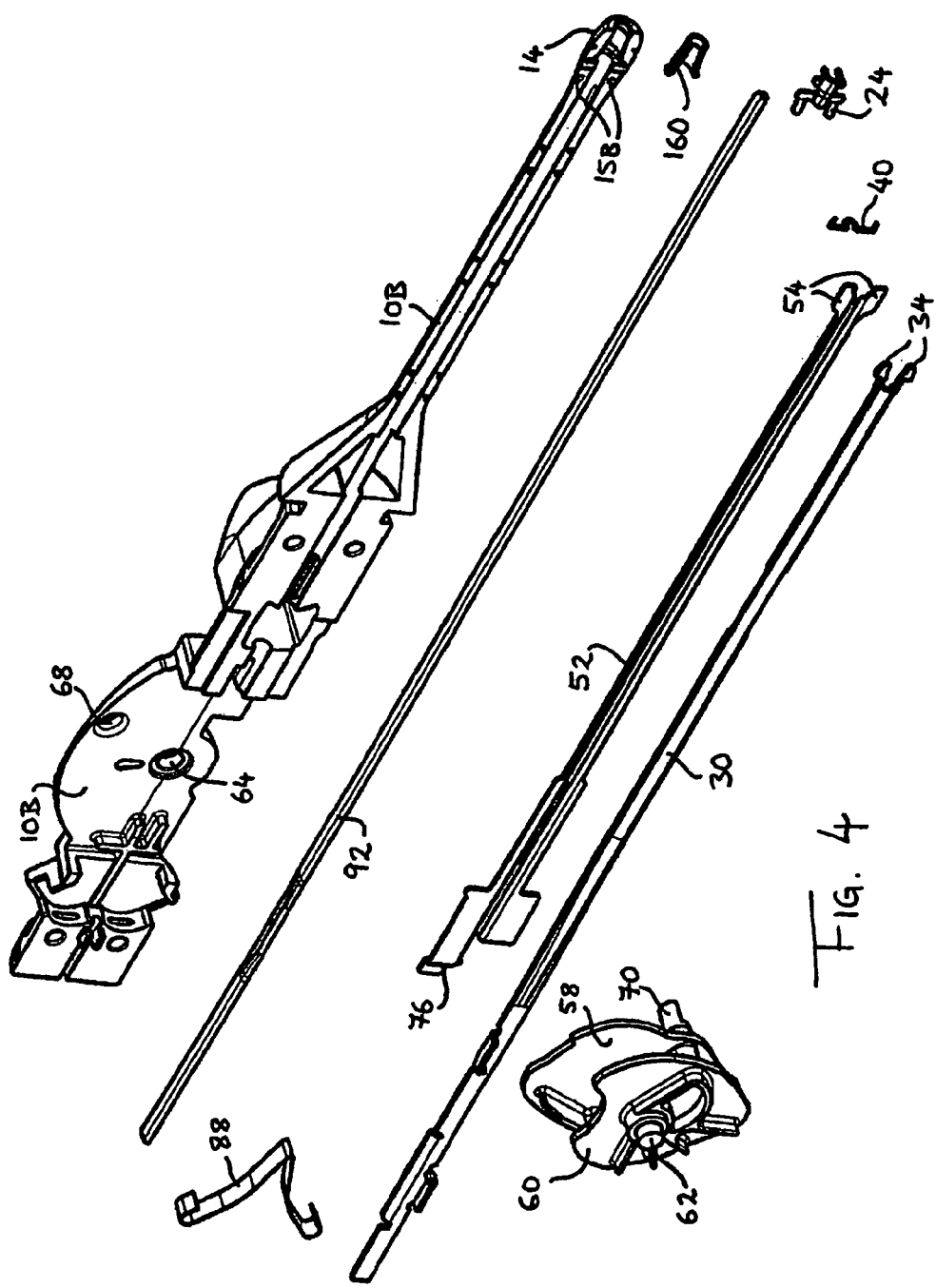
FIG. 4 is an exploded perspective view of the components seen in FIG. 3 further omitting the left-hand side handle.
Figure 5:
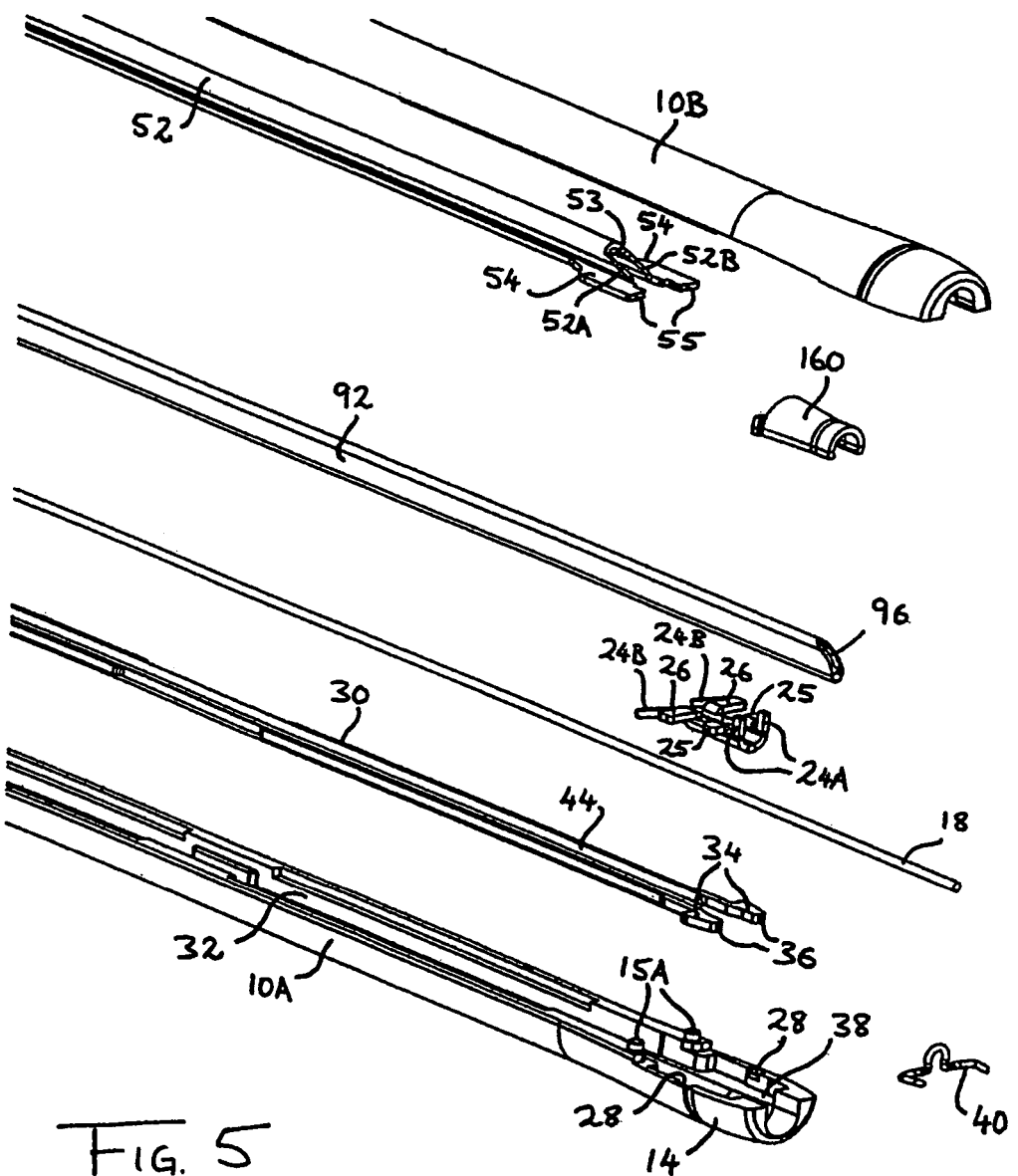
FIG. 5 is an exploded perspective view of the internal components at the free end of the shaft.

Referring to the drawings, an exemplary stapler can include a rigid shaft 10 extending from a moulded plastic housing 12 shaped in the form of a pistol-like handle. The shaft 10, which is hollow to accommodate various moving components to be described, comprises right and left-hand sides 10A, 10B respectively which are secured together at the distal free end by a section of heat shrinkable tubing 91 in combination with interference pins and mating cavities 15A and 15B (FIGS. 4 and 5) along the edges of the distal tip, and at the proximal end by pins 17A mating in an interference fit with corresponding cavities 17B (FIGS. 2 and 3) captured within the housing 12. Likewise, the housing 12 comprises left and right-hand sides 12A, 12B respectively.

The major part of the exposed length of the shaft 10 has a constant circular cross-section, but at its free end the shaft 10 has a portion 14 of increased diameter having a "bullet" profile. One end of this bullet portion 14 is tapered down toward a staple exit slot 16 while the other end is tapered down to the remaining section of the shaft, which extends back into the housing 12. The ratio of the maximum diameter of the bullet portion 14 to the diameter of the remaining section of exposed shaft is approximately 5:4. Heat shrink sleeve 91 sits flush with the surface of the bullet portion 14, to ensure a traumatic entry, percutaneously, into the tissue.

The reason for the bullet profile is so that the shaft 10 is as atraumatic as possible during introduction to the body to minimise the amount of force and tissue dilation required when tracking the device percutaneously over a guidewire 18 and onto the surface of a blood vessel adjacent a puncture hole, as will be described. In an alternative embodiment, not shown, the bullet portion 14 is oval in cross-section with the major axis of the oval being coincident with the staple exit slot 16, so as to minimise the circumferential length for a given staple width.

The bullet portion 14 of the shaft 10 houses a staple 40 and a staple delivery mechanism (FIGS. 4 to 7). The staple delivery mechanism comprises a tiltable anvil 24 and a pair of rod-like actuating members, namely an elongated anvil support 30 and an elongated staple former 52, the latter being slidable in the shaft 10 and operated by a trigger-operated cam mechanism 62 in the handle housing 12.

The anvil 24 has a pair of upstanding fingers 24A at the front and a pair of downwardly inclined tilt arms 24B at the rear. The anvil 24 is tiltably mounted in the bullet portion 14 by a pair of wings 26 which are pivotable in recesses 28 in the right-hand side 10A of the shaft 10 (the wings 26 are retained in the recesses by the underside of projections 54 on the former 52).

Figure 6:
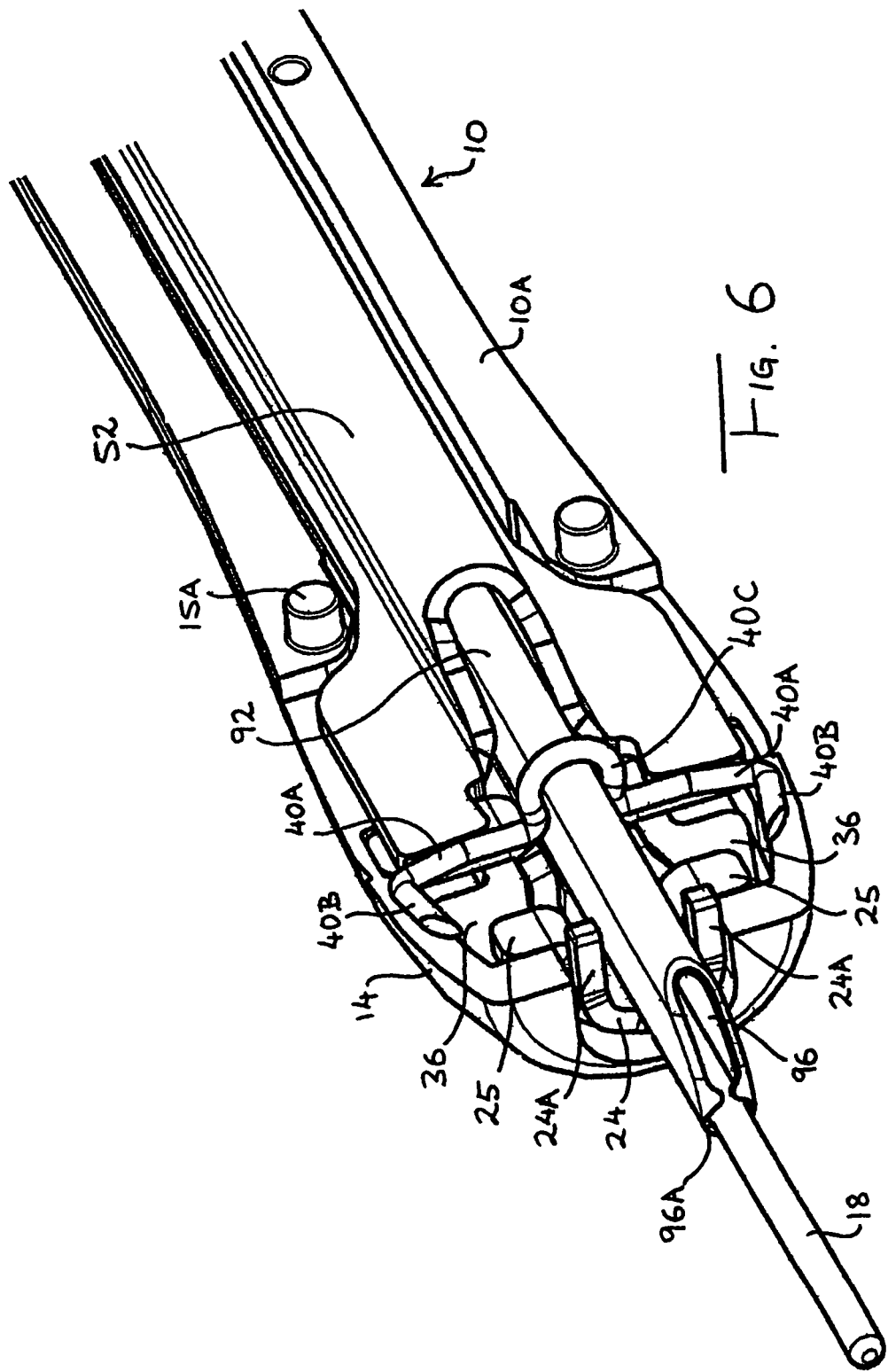
FIG. 6 is a perspective view of the internal components at the free end of the shaft in the pre-fire position and omitting the left-hand side of the shaft.
Figure 7:
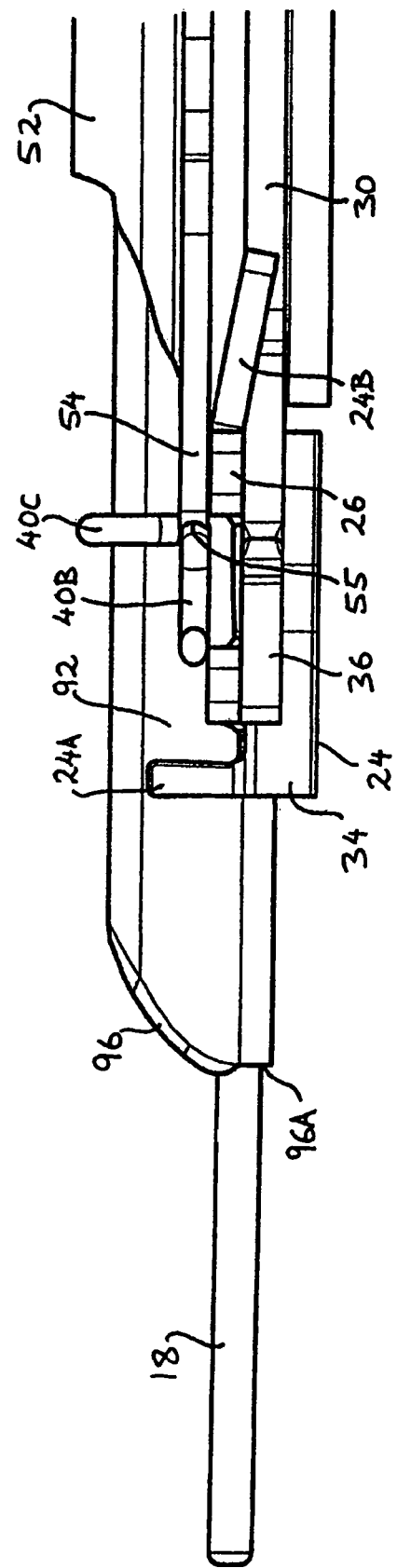
FIG. 7 is a side elevation of the components of FIG. 6 in the pre-fire position.
Figure 10:
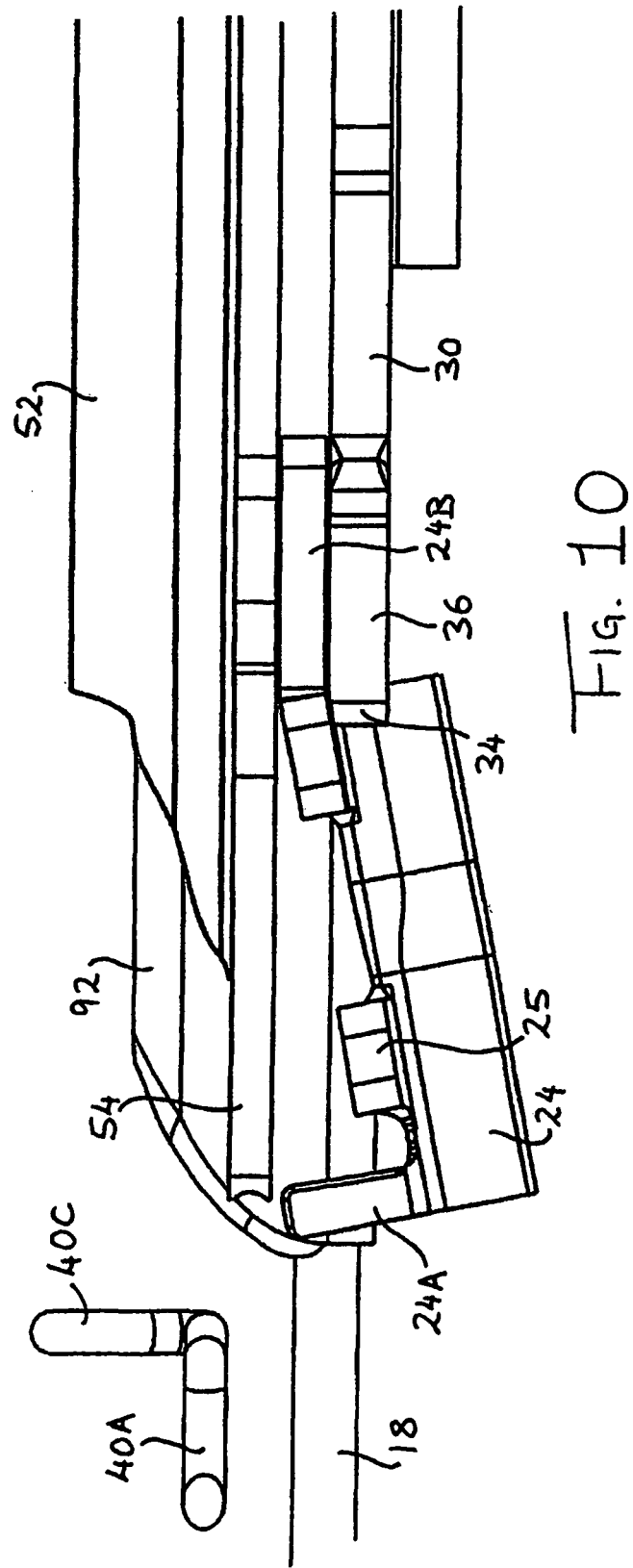
FIG. 10 is a side elevation of the components of FIG. 9 in the post-fire position.

Tilting of the anvil 24 is effected by the cam mechanism 62 via the anvil support 30, which is slidable axially within the right-hand shaft side 10A in channel 32. The front end of the anvil support 30 is bifurcated to form two arms 34 having lateral projections 36 (FIGS. 6 and 7). The arms slide in rebates 38 in the right-hand shaft side 10A. The anvil support 30 is movable, by the cam mechanism 62, from a forward position, FIGS. 6 and 7, wherein the arms 34 extend under the anvil's support wings 25 to support the anvil forming fingers 24A directly in front of a surgical staple 40 to be delivered, to a rearward position, FIG. 10, wherein the arms 34 are withdrawn under the downwardly inclined tilt arms 24B at the rear of the anvil 24 so as to tilt the anvil anti-clockwise (as seen in FIG. 10) and displace the fingers 24A out of the path of the staple 40. The angle of incline of tilt arms 24B may be increased to cause separation of the two shaft halves, in addition to displacing the fingers 24A out of the path of the formed staple, to aid in staple release. This is achieved by the anvil (in its fully tilted position) applying pressure to the underside of former 52 and the upper surface of the right shaft 10A.

Figure 11:
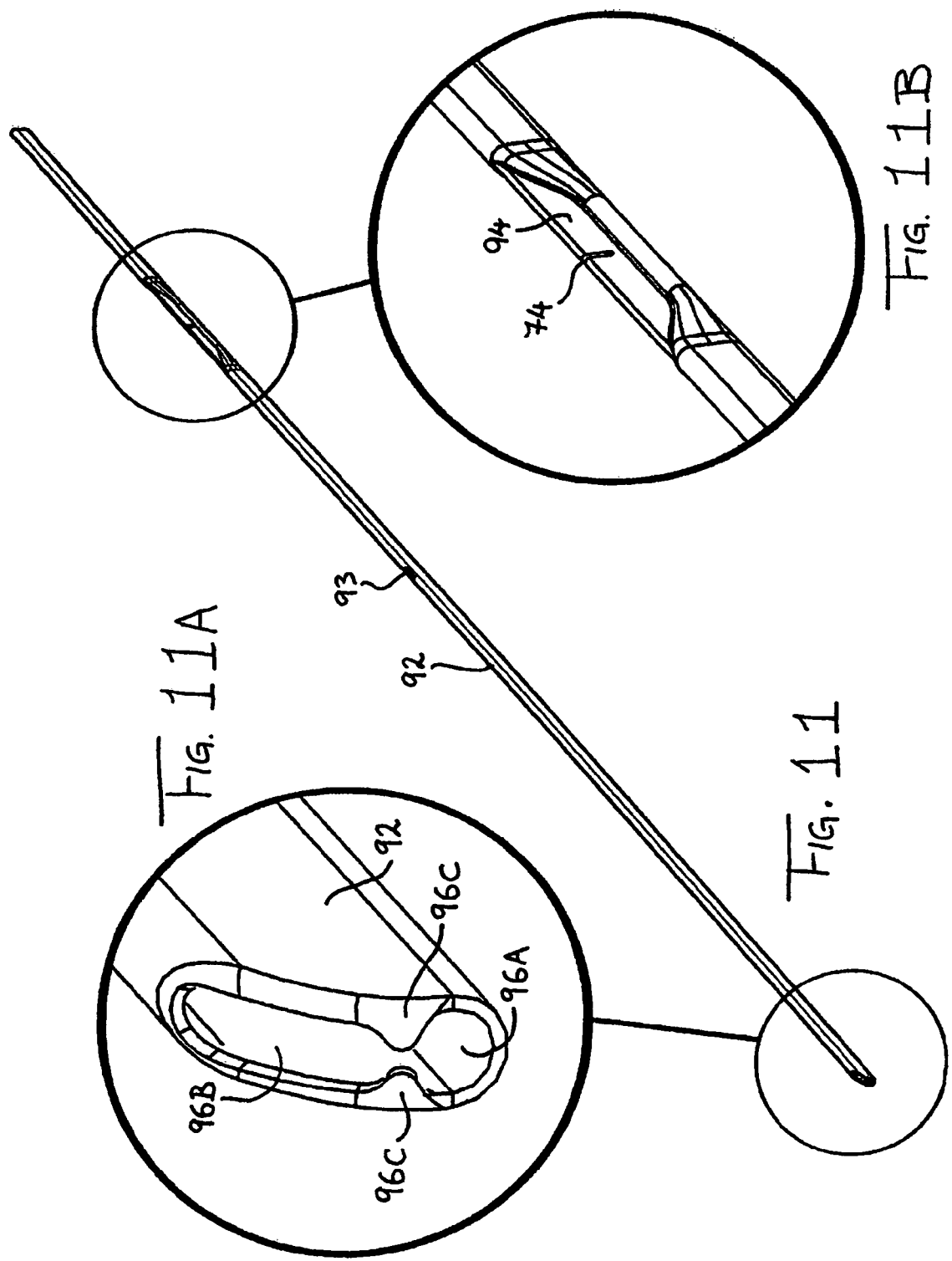
FIG. 11 is a perspective view of the blood locator tube with enlarged views of the front and rear portions, FIG. 11A and FIG. 11B respectively.

Referring additionally to FIGS. 11, 11A and 11B, a hollow blood locator tube 92 is slidable axially within the shaft 10 in a channel 44 in the anvil support 30 and in an opposing U-shaped channel 53 in the staple former 52. The tube 92 extends the full length of the shaft 10 and has a constant, generally oval or elongated cross-section, except at its distal tip 14 where the locator tube 92 is formed into a narrow opening 96 and at a crimped region 94 towards the rear of the tube 92 which is formed to allow only the guidewire 18 and not blood to exit the rear of the locator tube.

Figure 9:
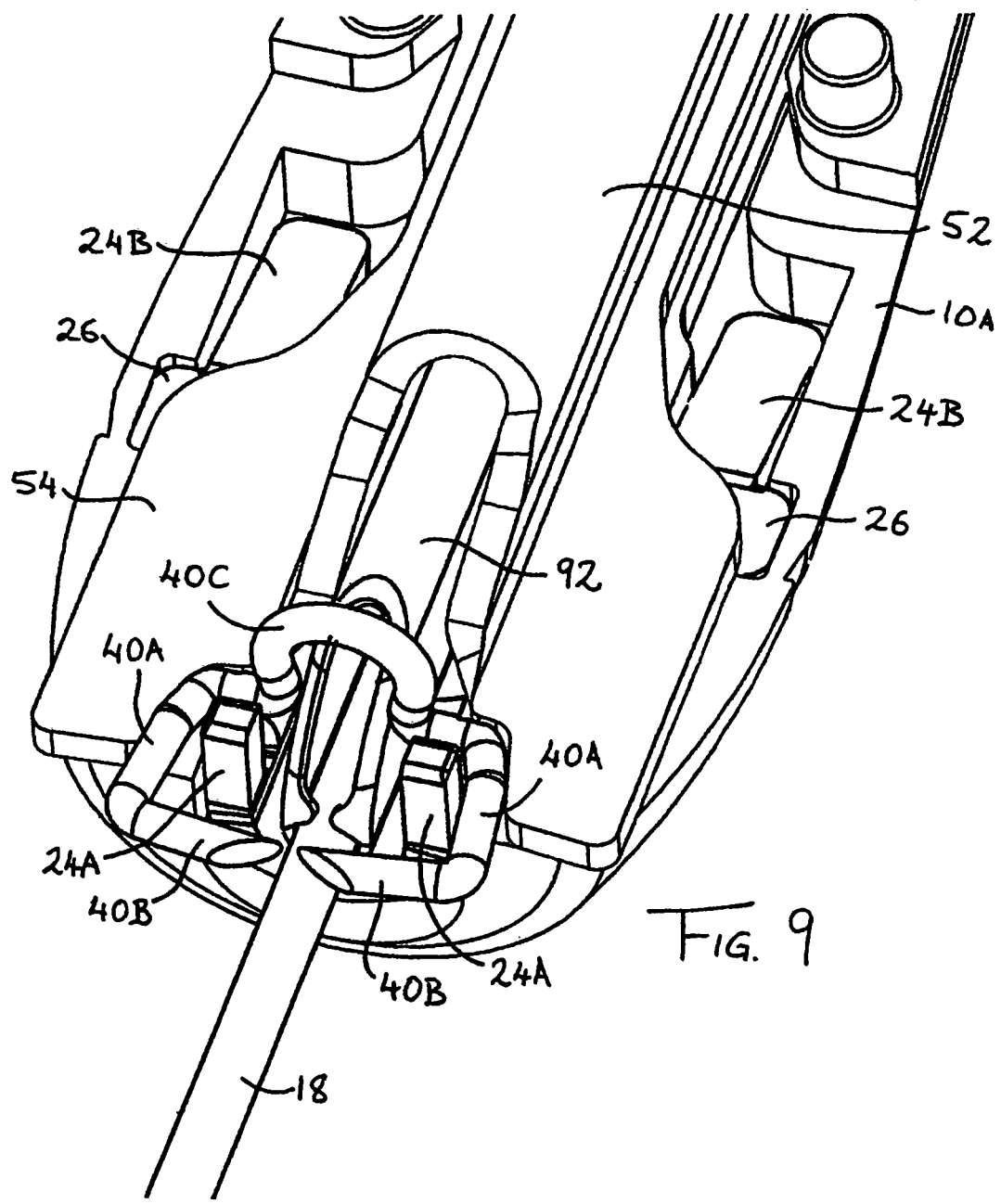
FIG. 9 is a perspective view of the internal components of the free end, showing the position of the components in mid-cycle with fully formed staple.

Under the action of the cam mechanism 62 the tube 92 is slidable axially in the shaft 10 between a forward position, FIGS. 6 and 7, wherein its front end projects beyond the bullet portion 14 of the shaft 10 under the influence of a leaf spring 88 to be described, and a rearward position, FIGS. 9 and 10, wherein the front end of the tube 92 is retracted within the bullet portion 14 behind the fingers 24A of the anvil 24 during the rotation of cam 62.

Figure 1:
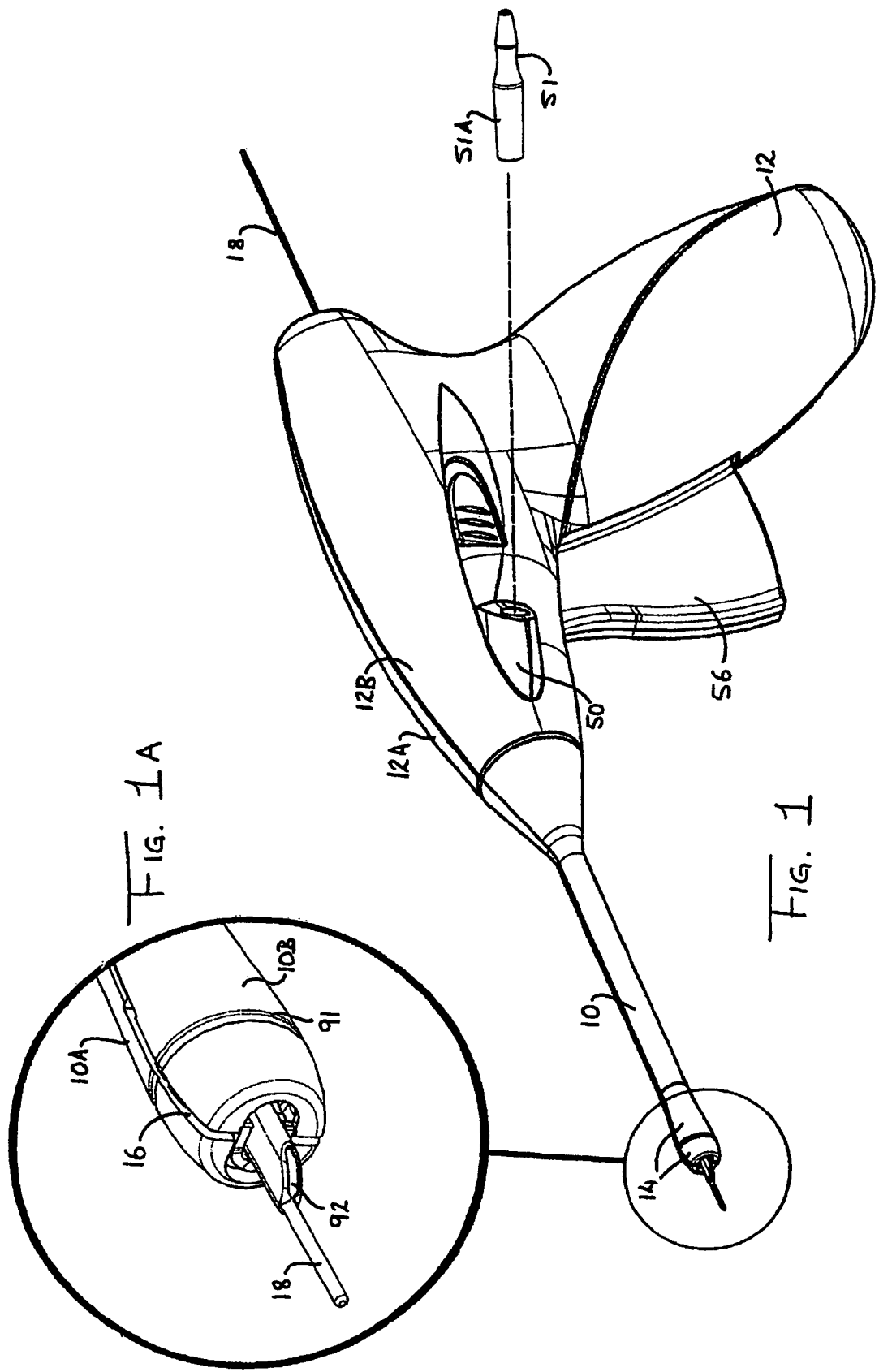
FIG. 1 is a perspective view of an embodiment of a surgical stapler according to the invention.

The purpose of the blood locator tube 92 is to follow a previously placed guidewire 18 to a puncture site in a blood vessel, thereby to locate the free end of bullet portion 14 of the shaft 10 against the exterior wall of the blood vessel at the puncture site. To properly locate the bullet portion 14 the front end of the tube 92 must actually penetrate the blood vessel wall at the puncture site and this is indicated by blood flowing back through the tube 92 and out through a blood outlet port 93 (FIG. 11) in the tube. A channel (not shown) in the part of the left-hand side 10B of the shaft 10 within the housing 12 provides communication between the port 93 and a blood exit port 50 (FIG. 1) on the side of the housing 12B, so that the blood flowing back through the tube 92 is visible at the exterior of the housing.

A blood exit port adapter 51 (FIG. 1) may be secured into the opening of the blood exit port 50 via a matching male luer taper 51A to enhance the visibility of the exiting blood. The blood exit port adapter has a reduced internal diameter, relative to the opening of the blood exit port 50, which for a constant blood flow increases the pressure of exiting blood causing a jet effect of exiting blood.

In the absence of the blood exit port adapter, the blood exit port's female luer taper opening matches that of the standard medical syringe's male luer taper making it possible at any time during the device's use to inject fluid via the blood exit port into the lumen of the locator tube to exit at its distal tip. This may be necessary from time to time to clear the locator tube's lumen of congealed blood and of trapped soft tissue. Alternatively, radiopaque contrast medium may be injected via the locator tube to confirm the relative location of the locator tube's distal tip to that of the blood vessel wall by fluoroscopy, or any injectable fluids may be injected for diagnostic or therapeutic reasons.

The blood outlet port 93 is sized to have a minimum area corresponding to the available blood entry area at the distal tip; however, is narrower (in a transverse aspect) than the diameter of the guidewire 18 to prevent the guidewire inadvertently exiting the blood outlet port during insertion, instead of exiting from the intended proximal end of the locator tube.

It has been found that the naturally formed shape of puncture wounds in arterial walls is elongated rather than round. Whereas the hole is formed by introducing instruments generally of round cross section, the wall tends to open generally along a transverse line which lies in the direction of the circumference of the artery (rather than along the axis of the artery). By having a generally oval blood locator tube, the locator tube (when introduced by the clinician with the major axis of the oval perpendicular to the axis of the artery), will fit more naturally within the arterial opening. The consequence of this is that the wound edges which are to be stapled together, lie closer together than if a tube of circular cross section were to be used.

This in turn has the consequence that the staple used need not be so large, and in turn, the dimensions of the shaft, which must accommodate the staple when in its unformed state, can be reduced, leading to less trauma for the tissue into and from which the shaft is introduced.

A further consequence of having a generally oval or elongated cross section for the locator tube is that the tube will be more disposed to the centre of the puncture than with a rounded tube. The present embodiment has a staple which straddles the locator tube, thereby increasing the likelihood of the staple closing the elongated wound at its centre rather than towards one or other of the extremities of the wound.

The opening 96 at the front of the tube 92 has an approximately circular portion 96A at the extreme forward tip of the tube which is of greater diameter than the width of the remaining portion 96B of the opening 96. The portion 96B is in the form of a slot which is aligned with the major axis of the elongated cross-section of the tube 92 and slopes rearwardly from the circular portion 96A. The guidewire 18, which passes through the tube 92, FIG. 11, is chosen to be of sufficiently smaller diameter than the diameter of the opening 96A at the front end of the tube 92 for the guidewire 18 to be easily inserted into the tube 92 and pass through the opening 96A. However, the guidewire is also chosen to be too large to fit within the remainder 96B of the opening 96. In this way guidewire 18 is constrained to remain in opening 96A, and the size of opening 96A sets an upper limit on the diameter of guidewire which can be used with the device. One could introduce a narrow neck or constriction into the opening 96 just above opening 96A (at the points indicated by 96C) to ensure that very small guidewires were constrained within the enlarged opening 96A, but in general this is unnecessary as the guidewire will normally be supplied with the device, or the device will only be supplied for use with a particular gauge of guidewire.

The rear crimp 94 and tip opening 96A are positioned to encourage the guidewire to lie along the bottom curved surface of the tube, i.e. that portion of the tube lying in a direct line between the opening in the crimped end and the opening 96A. This helps prevent guidewire 18 from laying up against the inside of blood exit port 93 and preventing egress of blood, FIGS. 11A and 11B.

The curvilinear nature of opening 96 increases the available inlet area to match that of the available area within the body of the locator tube with the guidewire 18 in situ.

The slot-like opening 96B slopes away from the circular opening 96A for ease of insertion into the vessel opening and to reduce the potential of trauma to the inner wall of the vessel opposite the opening being stapled. This is achieved because the guidewire 18 protruding from opening 96A will tend to push the opposite wall of the vessel away from the locator tube tip, and the point at which the guidewire protrudes (due to it being constrained in the opening 96A) is the farthest part forward of the tip. Thus, the shape of the tip is streamlined away from opening 96A to prevent any part of the tip gouging into or otherwise damaging the inner vessel walls. Also, the peripheral edges 95 of the opening 96 are bent inwardly to as to avoid sharp edges which might damage soft tissue and the vessel wall.

Figure 12:
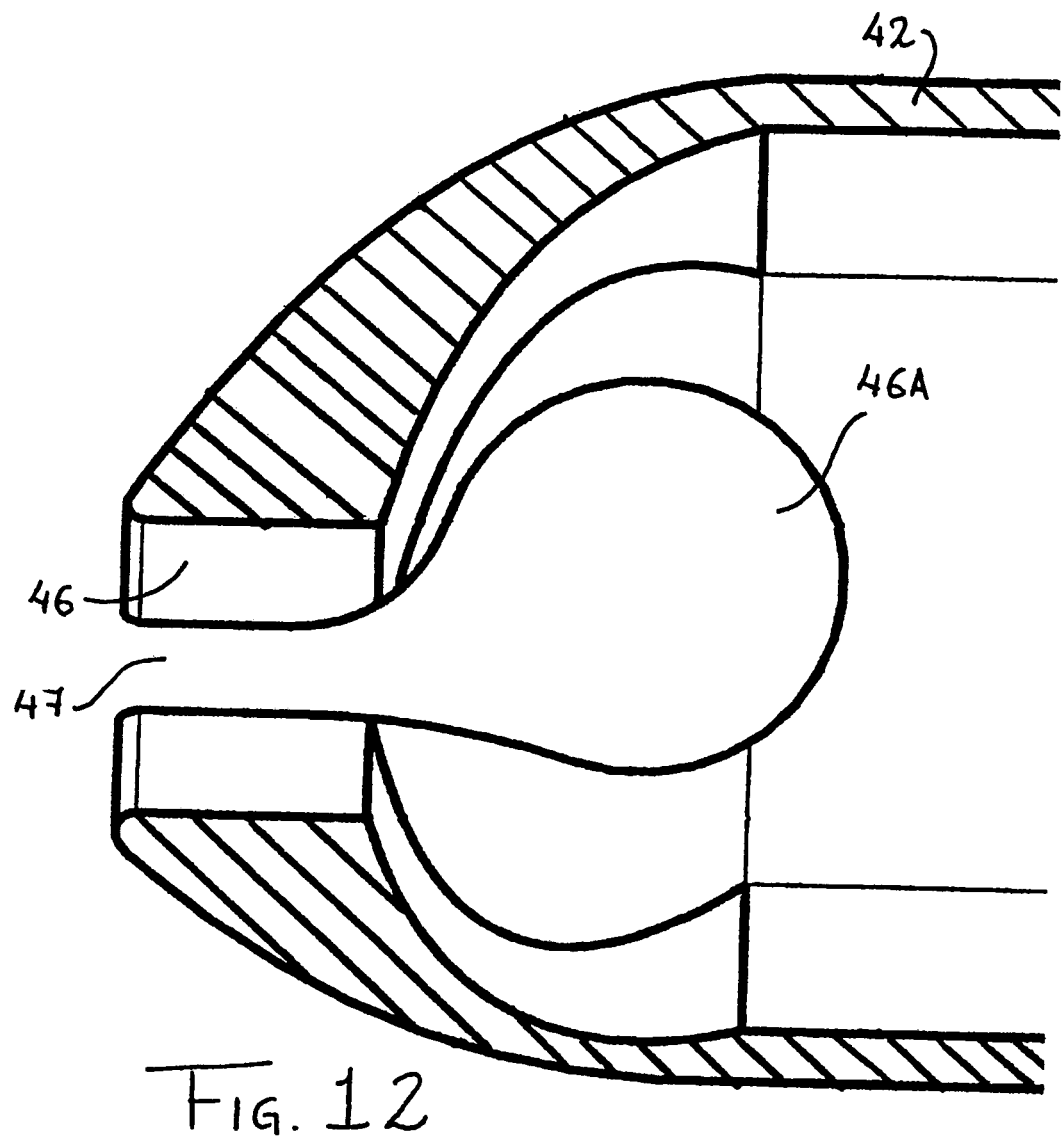
FIG. 12 is a side sectional elevation of the front portion of an alternative embodiment of the blood locator tube of the stapler.

The distal end of an alternative embodiment of a locator tube 42 is shown in FIGS. 12 and 13. This embodiment also has a substantially constant elongated cross-section, which in this case converges to an approximately circular guidewire opening 46 at the extreme forward tip of the tube. The guidewire 18, which passes through the tube 42, is usually chosen to be of sufficiently smaller diameter than the diameter of the opening 46 for there to be an adequate gap for the blood to pass back through the tube 42 even in the presence of the guidewire. However, further openings 46A are provided in opposite sides of the tube 42 just behind the front opening 46 to allow more ready access of the blood to the interior of the tube in cases where the guidewire 18 may not leave a large enough gap for passage of blood solely through the opening 46. The three openings 46, 46A, 46A in fact form respective portions of a single front opening, being in reality three connected lobes, all connected by constricted channels 47, and all in communication with the interior of the tube.

An alternative embodiment is shown in FIG. 13(A) where the three openings 46, 46A and 46A, while collectively constituting the front opening of the tube 42, are independent of each other. Again, opening 46 at the front of the tube is sized to receive a maximum size of guidewire and openings 46A are sized to allow a sufficient flow of blood to enter the locator tube.

A problem can arise in devices of this type where an oversized guidewire is used which occludes the hollow interior of the blood locator tube and thereby prevents blood flow back through the tube. To prevent this situation the lobe 46 through which the guidewire emerges in the tip of the tube of FIGS.

12, 13 and 13A is of a lesser diameter than the internal bore of the tube. The dimensions of this lobe 46 set a maximum for the guidewire diameter for use with the device, and ensure that even when this maximum diameter guidewire is used, there is still sufficient internal clearance within the tube bore to allow a strong blood flow through the tube from the other lobes 46A.

Figure 8:
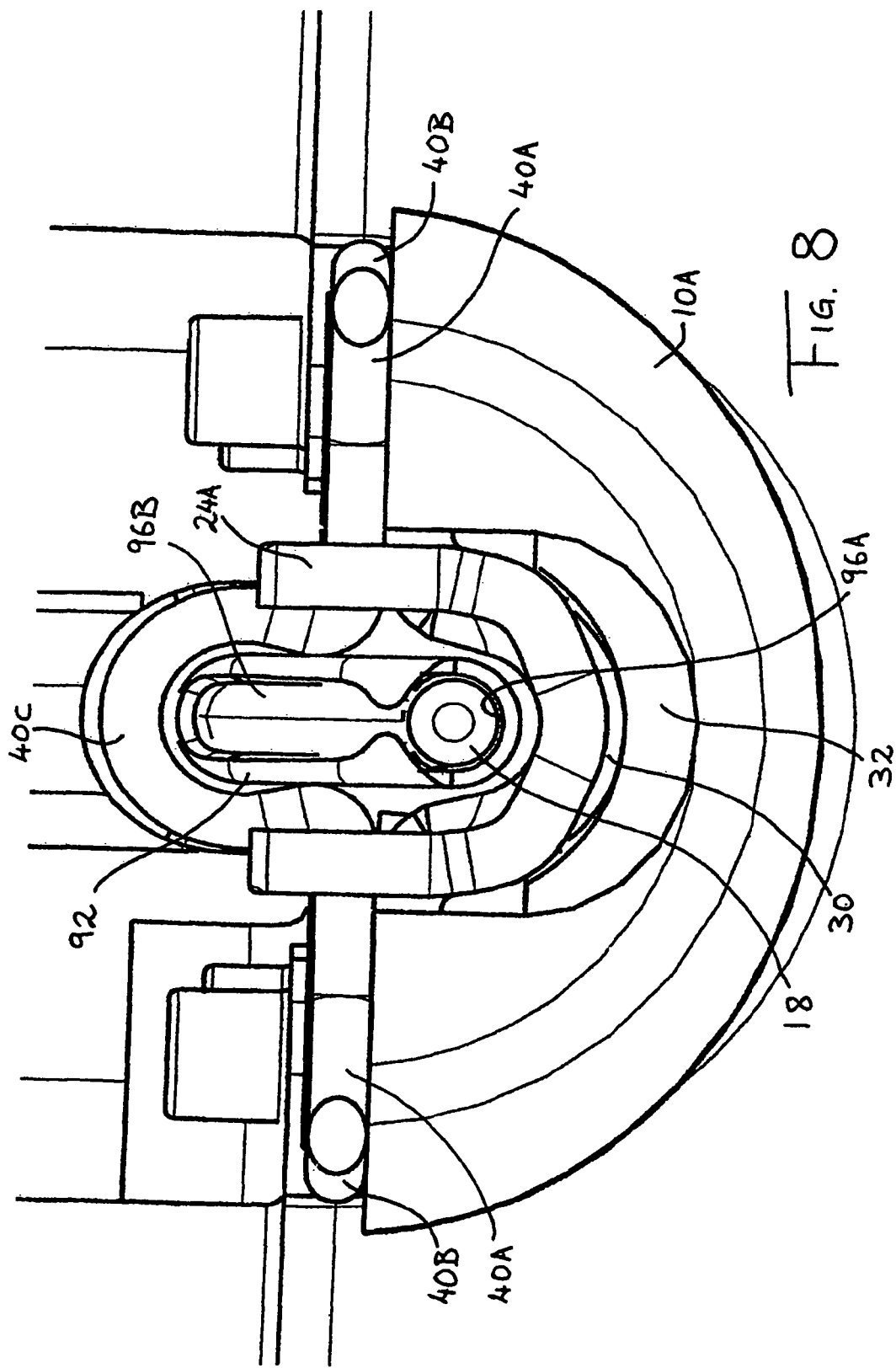
FIG. 8 is a front elevation of the components of FIG. 6 in the pre-fire position.

The staple 40 straddles the blood locator tube 92 within the bullet portion 14 of the shaft 10, see FIGS. 6 and 8, and is slidable thereon forwardly towards the free end of the bullet portion 14. In particular (see also the enlarged view of FIG. 14), the staple 40 comprises a back or base portion 40A from which extend perpendicularly at each end respective legs 40B which terminate in sharpened points. The base portion 40A and legs 40B lie in substantially a common plane except for a centre portion 40C of the base portion 40A which is deformed in a direction perpendicular to the legs 40B so as to have an Ω (omega) shape generally complementary to the external cross-sectional profile of the blood locator tube 92 and internal cross-section of an insert 160, to be described. The base section 40A is pre-bent to between 150° and 170° at points A and B equidistant from the centre of the base, positioned to maximise the closure of the closed staple (and is relevant to the depth of forming wings 54 on the former 52). The base section is also deformed at points C & D so as to narrow the cross sectional width of the wire at both points thereby directing the staple to bend at these points. The staple 40 is mounted on the blood locator tube 92 such that the centre portion 40C of the staple sits on the upper half of the tube 92, as seen in FIGS. 6 and 8, where the narrow open section of the omega shape is approximately equal to the width of the tube and with the legs 40B pointing forwardly on opposite sides of the tube 92. The depth of the centre portion 40C of the staple 40 is such that the legs 40B of the staple lie substantially directly on opposite sides of the central axis of the tube 92. This will ensure that the staple 40 is positioned centrally across the puncture hole in the blood vessel. In order to avoid the guidewire 18 fouling the staple 40 when the latter is closed on the puncture site, the hole 96A is offset below the plane containing the legs 40B of the staple, FIG. 8.

Figure 18:
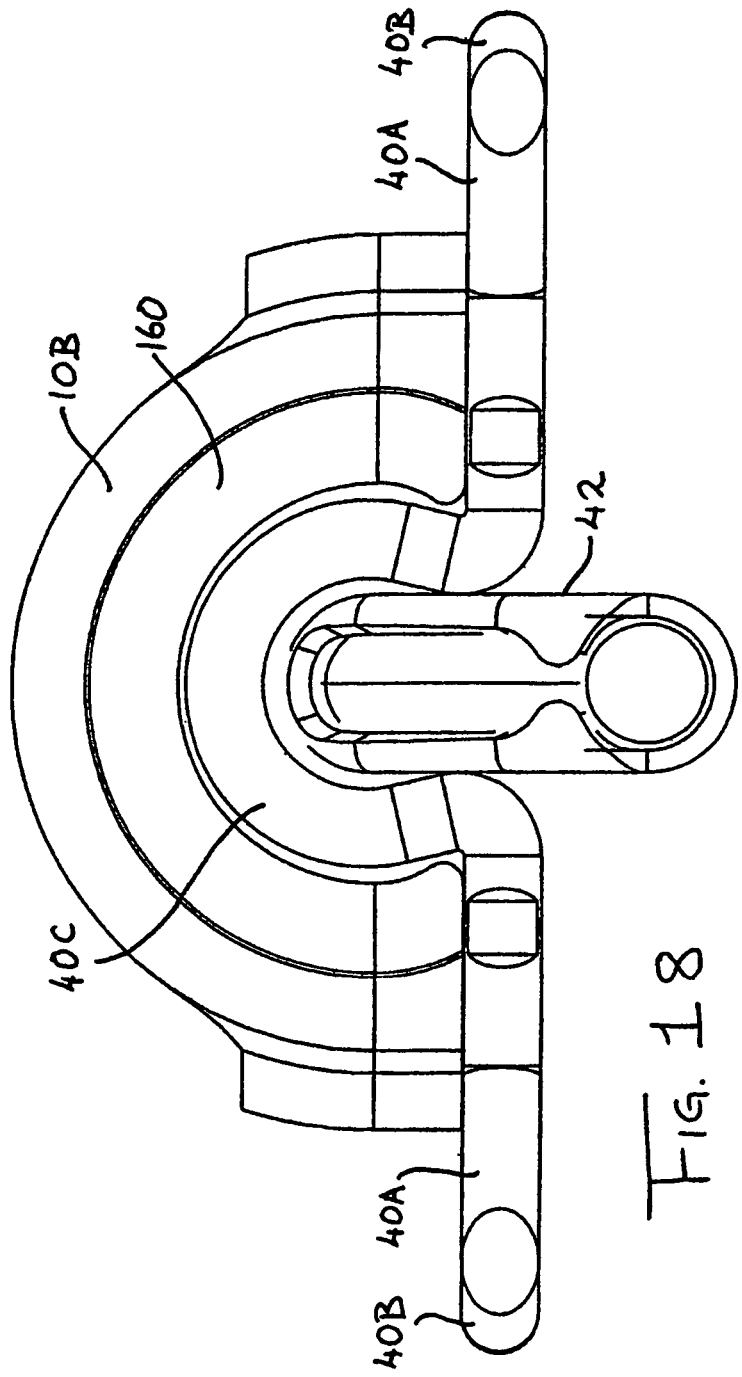
FIG. 18 is an end view of the surgical staple, locator tube and insert.

The metal insert 160 is received in a recess in the left-hand shaft side 10B within the bullet section 14. The insert 160 provides mechanical support for the omega section 40C of the staple 40 during the staple forming process and is engaged by the former 52 during the staple ejection phase of the process so as to separate both halves of the bullet section for easy staple release. The insert is profiled to generally correspond with the external profile of the omega shaped portion 40C of the staple. At the distal end the insert profile tapers down to closely approximate the omega-shaped portion of the staple 40C (FIG. 18). This has the effect of offering mechanical support to the omega-shaped portion of the staple during the staple forming process, during which the base section is bent about the anvil fingers. This bending motion in turn causes the omega to open up or flatten out. The metal insert prevents this from happening only allowing the staple base to deform around the anvil. The omega interlock system between the staple 40 and insert 160 (FIG. 18) also stabilises the staple, vertically, within the staple exit plain during the forming process, whilst allowing easy staple release once formed, due to the relatively small contact area between staple and insert.

The staple former 52 has a cross-section conforming to that of the blood locator tube 92 and is slidable on the blood locator tube 92 axially within the shaft 10. The former 52 is located behind the staple 40 on the tube 92 and is operated by the cam mechanism 62. At its front end the former 52 has a pair of forming arms 54 which are so shaped that, when the former 52 is driven forward by the cam mechanism 62, the staple 40 is driven against and deformed around the anvil fingers 24A so that the legs 40B of the staple close together (FIG. 9) onto the puncture site. The surface of the forming arms which contact the staple 55 may be so profiled to match the cross-sectional geometry of the staple. This matching profile stabilises the staple on the forming surfaces of the forming arms 54 during the high pressure contact with the staple during staple forming and closure. During the forward movement of the staple, the staple legs slide toward the anvil 24 along a track defined by the staple exit slot 16 between the opposite halves the bullet portion 14. The slot 16 provides a slight interference fit on the staple legs 40B to prevent the staple 40 moving forward during storage of the device or prior to firing. The slot 16 further prevents the staple rotating in the horizontal plane (FIGS. 7 and 10) during its forward travel. Once forming of the staple around the anvil is completed the forming force is removed from the former 52 by a drop-off in the cam, the anvil is lowered and the former advanced again to eject the staple from the device. During this forward movement (ejection phase), the sloped edges 52A and 52B of the former engage with the metal insert 160 to prise open the bullet section of the shaft assembly thus facilitating staple release.

Figure 3:
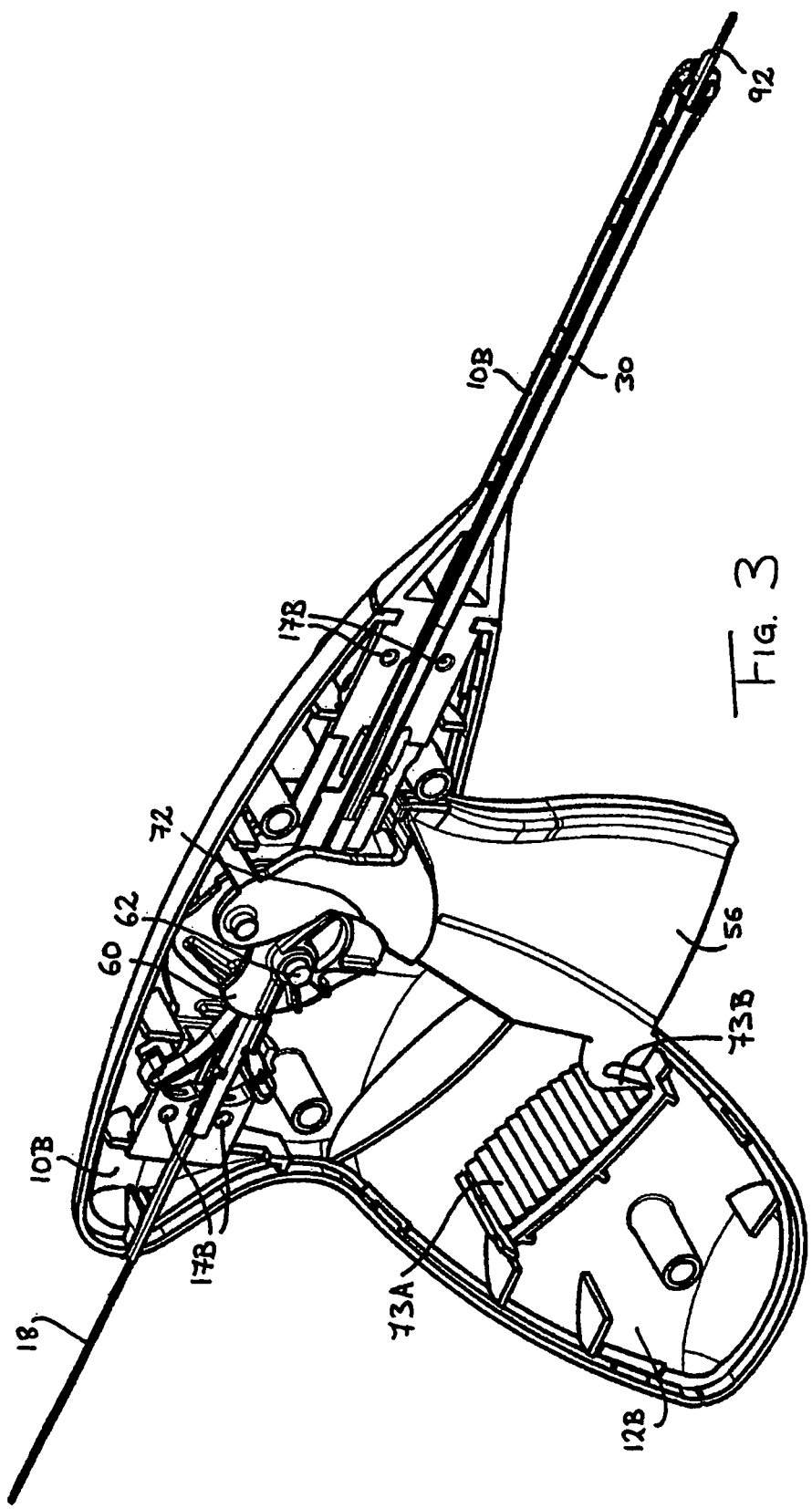
FIG. 3 is a perspective view of the stapler of FIG. 1 with the right-hand side handle and shaft removed.
Figure 16:
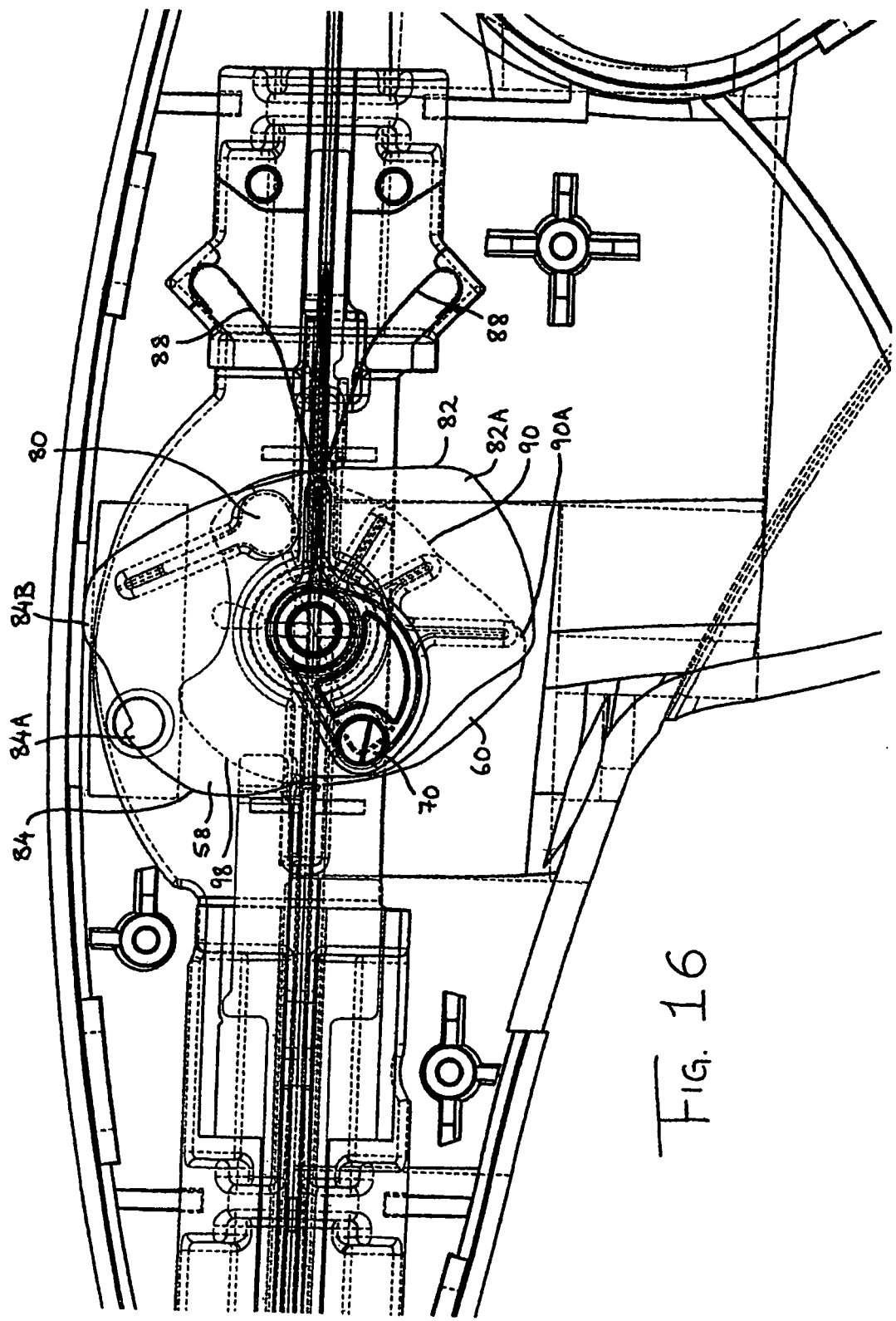
FIG. 16 is a side elevation of the cam mechanism.

The cam mechanism 62 can be seen in FIG. 3 and in enlarged views of FIGS. 15 and 16. The mechanism 62 consists of a first cam 58 and a second cam 60 mounted on a common axis 62 which sits in a recess 64 in the left-hand side 10A of the shaft (FIG. 4) and a corresponding recess (not shown) in the right-hand side 10B. Trigger 56 is similarly mounted in the shaft by a pair of stub axles 66 which are received in a trigger seating recess 68 in each half of the shaft 10, FIG. 4.

An actuating pin 70 extends through the first and second cams 58, 60. This actuating pin is acted on by a cam actuating surface 72 (FIG. 3) provided on the trigger 56, so that when the trigger is squeezed the actuating surface moves the actuating pin in an anticlockwise direction around the axis 62. Because the actuating pin extends through both cams 58, 60 of the mechanism 62, the cams are both rotated simultaneously through the same angle as determined by the trigger squeeze. The use of this cam mechanism ensures accurate timing and positive mechanical displacements of all the moving components and accurate movement of the components relative to each other. The geometry of the trigger pivot pins 66 and actuating surface 72 relative to the cam pivot 62 and cam actuating pin 70 is configured to minimise the trigger rotation to only 23 degrees whilst the cam rotates a total of 90 degrees. This configuration also provides a mechanical advantage that the trigger delivers to the cam-actuating pin 70 of approximately 1:4. This geometry is further configured to deliver the best mechanical advantage at the phase during the staple forming cycle, which requires the highest forming forces, having the advantage of minimising the trigger effort and ensuring a constant trigger effort over the full cycle. Trigger 56 further comprises a ratchet lever 73B, shown in FIG. 3, which engages with ratchet strip 73A, which is mounted in the right handle 12A, FIG. 3. This non-return ratchet system ensures the firing cycle of the staple is uninterrupted, non-repeatable and provides a positive indication that the device has been used.

Referring back to FIG. 3, a leaf spring 88 positioned in a recess in the left-hand side 10A of the shaft and a corresponding recess (not shown) in the right-hand side 10B. The free ends of the spring are formed into a loop so as to pivot freely in the curved corner recesses in which it sits and to aid assembly. The apex of this spring is positioned in a slot 74 in the crimped portion 94 of the blood locator tube 92 thus assuming the role of cam follower for the blood locator tube. This blood locator tube cam follower 74 is acted on by the first cam 58. Similarly, the first cam 58 acts on a former cam follower 76, whereas the second cam 60 acts on anvil-support cam followers 78A and 78B. The shape of the first and second cams 58, 60 are shown in elevation in FIG. 16 (the second cam 60 is shown in dotted outline as it is concealed by the first cam). FIG. 16 also shows actuating pin 70, and a reinforcing strut 80 mounted between the first and second cams diametrically opposite the actuating pin 70.

The cams are shown in the starting positions in FIGS. 15 and 16. Squeezing the trigger fully (through an angle of 23 degrees) causes the cams to rotate anticlockwise through 90 degrees.

The apex of the leaf spring 88 which engages with and operates as a cam follower for the blood locator tube (leaf spring apex) acts against the rear surface 82 of the first cam 58. As the first cam rotates anticlockwise from the position shown in FIG. 15, the distance between the blood locator tube cam follower 74 and the axis 62 is increased. This causes the blood locator tube to be drawn backwards as the trigger is squeezed.

The former cam follower 76 acts against the front surface 84 of the first cam 58. Again the distance between former cam follower 76 and axis 62 increases through the initial stages of the trigger being squeezed. The profile of surface 84 is designed with two distinct non-linear efficiencies, transitioned from low mechanical efficiency/high displacement to high mechanical efficiency/low displacement. The first rise rate being for displacement of the staple from its starting position to initial forming against the anvil, which requires the largest displacement of the staple with minimal load. The second non-linear rise rate is designed to correlate the cams mechanical efficiency with the load profile required to form the closed staple, minimising the trigger effort required and ensuring a constant trigger effort over the full cycle. A V-shaped section 84A of front section 84 causes the former 52 to momentarily suspend its forward motion when the staple has been fully formed. The effect of this is to momentarily release the pressure off the formed staple against the anvil, allowing the anvil to be dropped. The geometry of the distal tip of the former is designed to provide sufficient intrinsic spring tension to allow the forming arms 54 to further squeeze the formed staple, once the anvil has dropped, to further closed the formed staple. As the cam continues to rotate the raised profile 84B on the cam causes the former to advance forward again, ejecting the staple clear of the device.

It can be seen that a raised hump 82A on the profile of the rear surface 82 of the first cam is located almost diametrically opposite the V-shaped section 84A. The reason for this is to increase the rate at which the blood locator tube is drawn out of the puncture site just before the staple is fully formed and released. The intention is to leave the tube in the puncture as late as possible to provide support for the walls of the blood vessel for as long as possible And also to ensure that the head of the device remains centred over the puncture hole. The blood locator tube 92 is biased forward by the blood locator tube leaf spring 88 which also maintains pressure between the apex of the spring and the rear surface 82 of the first cam 58.

The blood locator tube leaf spring 88 allows the locator tube to be displaced in a proximal direction (back into the shaft of the device) against the spring tension in the event that the locator tube meets any significant resistance during insertion of the device, to prevent unnecessary trauma to soft tissues, the vessel or its rear wall.

An example of where this is particularly useful is if the stapler is advanced too far into the vessel, so that the tip of the tube 92 meets the inner wall. The blood locator tube will then be displaced back into the shaft, and may be designed to protrude through the end of the handle housing to give a visual indication that the device has been inserted against the wall. Furthermore, the device may be designed so that the blood outlet port 93 on the tube 92 is brought out of registry with the blood exit port 50 in the handle housing when the tube is displaced backwards, so that the clinician will note the flow of blood ceasing when the tube meets the inner vessel wall in this way.

The cam mechanism 62, however, provides positive mechanical displacements for withdrawing the locator tube at the appropriate timing, to ensure there is no chance of the staple being formed whilst the locator tube is in a forward position and potentially interfering with the staple formation.

A further reason to leave the blood locator tube in the puncture hole as late as possible is that the continued retraction of the tube everts or turns outwards the opposed edges of the puncture wound and aids penetration of the staple legs into the arterial wall. Eversion of the edges of the puncture helps prevent thrombus formation within the vessel. Yet another reason to leave the blood locator tube in the puncture hole as late as possible is to ensure that the stapler head remains centred over the hole during the staple delivery process. When the locator tube is fully retracted, only the guidewire is left within the wound, and this will be easily retracted from the closed wound after the stapler has been removed from the puncture site.

The anvil-support cam follower 78B acts against the rear surface 90 of the second cam 60. It can be seen that this rear surface 90 provides the greatest increase in distance relative to the axis to the section 90A from about 60 to 90 degrees below the horizontal. The reason for this is that the anvil is maintained in place until the staple has been formed and the pressure on the former has been relaxed slightly to allow the anvil to drop. The anvil is maintained in place for the initial 60 degrees of rotation by the anvil-support cam follower 78A being in contact with cam surface 98 of cam 60, preventing the anvil-support 30 from moving from its starting position. The cam surface 98 for the first 60 degrees of cam rotation is at a constant distance from the cam axle 62 (in dwell).

In use, the stapler is initially in the "pre-fire" configuration shown in FIGS. 6 to 8. The front end of the blood locator tube 92 is in a fully forward position projecting beyond the free end of the bullet portion 14 of the shaft 10, the anvil-support 30 is in a fully forward position with its arms 36 extending under the anvil's support wings 25 ensuring the anvil fingers 24A are directly in front of the staple 40, the former 52 is in a fully retracted position away from the anvil fingers 24A, and the staple 40 is in its fully back position up against the forming arms 54.

In this configuration the external end of a previously positioned guidewire 18 is inserted into the hole 96A in the front end of the blood locator tube 92 and fed through the tube 92 until it exits a guidewire exit port at the rear of the housing 12. The stapler is now fed along the guidewire 18 until the tip 95 of the tube 92 enters the blood vessel lumen through the vessel's puncture hole. This is indicated by blood flowing out of the blood exit port 50 or, if present, the adapter 51. At this point the front end of the bullet portion 14 of the shaft 10 will be resting against the exterior wall of the blood vessel.

Now the trigger 56 is squeezed, causing the cams of the cam mechanism 62 to rotate through 90 degrees. As mentioned, the rear end of each of the blood locator tube 92, anvil-support 30 and former 52 are coupled to the cam mechanism via cam followers and the following co-ordinated movement of these components takes place as the cams rotate through 90 degrees.

(A).

0 degrees: Stapler in pre-fire configuration.

32 degrees: Former 52 forward sufficiently to clamp staple against anvil fingers 24A, blood locator tube begins to retract. At this point the staple legs will have punctured the wall of blood vessel, but the staple is not yet fully deformed.

50 degrees: Former 52 forward sufficiently to deform the staple legs around the anvil fingers 24A and close the staple on the puncture site: blood locator tube 42 fully retracted. At some point between 32 and 50 degrees, the blood locator tube will have withdrawn from between the staple legs in time to allow them to close. This should be left as late as possible to provide support for the walls of the blood vessel for as long as possible.

65 degrees: Clamp force released from staple (due to drop off in cam profile). Anvil support 30 starting to retract.

75 degrees: Anvil support 30 retracted sufficiently to act against anvil sloped tilt arms 24B. Anvil fingers 24A begin to drop.

83 degrees: Anvil support 30 fully retracted. Anvil fingers 24A dropped down to allow release of staple. Intrinsic tension in former arms 54 further closes the staple. Former 52 begins to move forward again to eject staple. Former 52 begins to interfere with the insert 160 to spread bullet portion 14 of the shaft to allow for clear staple release.

90 degrees: Former 52 fully forward; staple ejected from the device.

The use of cams in cam mechanism 62 ensures the accuracy of sequence and relative timing between events as well as ensuring positive mechanical displacements of all components.

In a further embodiment to the above described device, on the completion of the cycle described above, further rotation of the cam causes the anvil support 30 to return to its fully forward position, lifting the anvil fingers 24A to their raised position behind the formed staple being held in forming arms 54. The former is then retracted in a proximal direction (back into the shaft) causing the rear of the closed staple to crash into the raised anvil fingers 24A, to be positively ejected from within the forming arms 54 and the device. The additional movements of the anvil support and former may be facilitated by additional cam lobes on cam 58; or alternatively spring driven, assisted and timed by appropriately positioned radial slots in cam 58 to allowing the cam follower of the anvil support to move forward and the cam follower of the former to move rearwards.

In a further embodiment the trigger activates an automatic firing cycle, not shown. A tension spring attached to the cams is released from its extended state so as to rotate the actuation cam through a 90 degree arc causing the same component movements as described above.

In an alternative embodiment, not shown, once the staple has been formed the forward end of the former 52 retracts and engages pull arms on the anvil-support 30 causing it to move in a rearward direction. As it does so, it engages with the rear end of the anvil 24, which is angled downward into the path of the moving slide. Centrally opposed wings extend from the anvil and are located so as to pivot in opposed wing slots formed in the right-hand side 10A of the shaft. Once engaged with the slide the rear end of the anvil is pushed upward causing it to pivot about the wings and arc the forward end of the anvil downward. As it does so, it disengages from the staple so that the device can be removed from the puncture tract along the guidewire.

In a further embodiment the reverse profile 82 on the first cam 58 which engages with the cam follower 74 on the blood locator tube 92 is extended so that when the staple forming cycle is completed the first cam continues to rotate causing the blood locator tube to move further in a proximal direction. At its distal end the blood locator tube has wings which as it moves in a proximal direction engages with the pull arms of the anvil-support 30 causing it to move in a proximal direction and engage the anvil tilt arms thereby disengaging the distal end of the anvil from the formed staple. In this embodiment the second cam is redundant and can be omitted.

Figure 17:
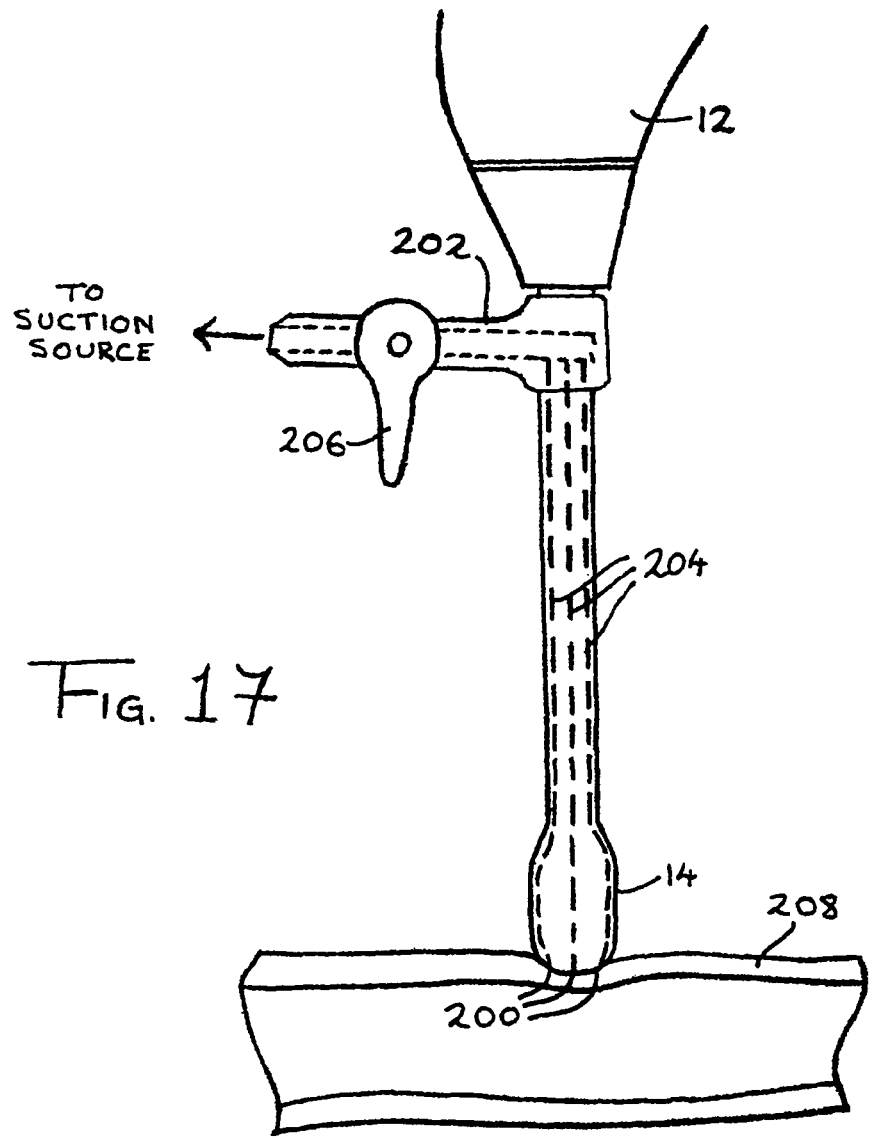
FIG. 17 is a side elevation of the shaft section of the device and suction port.

In a further embodiment, FIG. 17, the bullet head 14 of the shaft 10, which approximates the blood vessel wall 208, includes a number of suction ports 200. These ports are in communication with a suction adapter 202 via capillaries 204 within the shaft section. Suction, from a standard wall suction outlet or independent suction pump, is supplied to the suction adapter 202 via an on/off tap 206. Once the device is in position on the arterial wall, as indicated by blood flowing from the blood exit port, the tap 206 is turned to the "on" position thereby delivering suction to the ports 200 on the bullet head 14. This in turn suctions the blood vessel wall 208 against the face of the head 14 so as to stabilise it during delivery of the staple. Once delivered the suction is deactivated so as to remove the device from the blood vessel wall and tissue tract.

The invention is not limited to the embodiments described herein and may be modified or varied without departing from the scope of the invention.

What is claimed is:

1. A surgical stapler comprising:
    a shaft;
    a locator received within the shaft and having a lumen configured to receive a guidewire, the lumen including a fluid outlet port and a guidewire exit port and including a distal opening forming both a distal fluid inlet port and a distal guidewire entry port, the fluid outlet port and guidewire exit port being in fluid communication with the lumen with the fluid outlet port being distal the guidewire exit port, the lumen extending from a proximal end of the shaft to a distal end of the locator, the locator being slidably movable with respect to the shaft between a forward position in which the locator projects beyond a free end of the shaft to enter a puncture site in a liquid-carrying vessel and thereby locate the free end of the shaft at the puncture site, and a rearward position in which the locator is retracted relative to the shaft; and
    a trigger configured to drive a staple through the shaft and simultaneously retract the locator such that the locator is withdrawn from between legs of the staple in time to allow the legs of the staple to staple together opposite edges of the puncture site.

2. The surgical stapler of claim 1, further comprising a staple having forwardly pointing legs disposed respectively on opposite sides of the locator.

3. The surgical stapler of claim 1, wherein the trigger is coupled to a housing formed on a proximal end of the shaft.

4. A surgical instrument for closing a puncture in a liquid-carrying vessel, comprising:
    a shaft;
    a locator received within the shaft and having a lumen configured to receive a guidewire, the lumen including a fluid outlet port and a guidewire exit port and including a distal opening forming both a distal fluid inlet port and a distal guidewire entry port, the distal fluid inlet port and the distal guidewire entry port being substantially coterminous with a distal end of the locator, the fluid outlet port and guidewire exit port being in fluid communication with the lumen and longitudinally separated one from another and the fluid outlet port being distal the guidewire exit port, the locator being slidably movable with respect to the shaft between a forward position in which the locator projects beyond a free end of the shaft to enter a puncture site in a liquid-carrying vessel, and a rearward position in which the locator is retracted relative to the shaft; and a trigger configured to drive a closure device toward the puncture site and to substantially simultaneously retract the locator such that the locator is withdrawn from the closure device to allow the closure device to close the puncture.

5. The surgical instrument of claim 4, further comprising a housing, the shaft extending distally from the housing and the trigger being located on the housing, the lumen extending from a proximal end of the housing to a distal end of the locator.

6. The surgical instrument of claim 4, the closure device disposed around the locator and having at least two tissue-penetrating legs formed thereon.

7. The surgical instrument of claim 6, wherein the at least two tissue-penetrating legs of the closure device are movable between a first, pre-deployed position, wherein the legs are substantially parallel to one another, and a second, deployed position wherein the legs extend toward one another.

8. The surgical instrument of claim 6, wherein the closure device is a staple.

9. A surgical instrument for closing a puncture in a liquid-carrying vessel, comprising:

a shaft having a locator slidably disposed therein, the locator having a lumen configured to receive a guidewire and being adapted to extend forward of the shaft to be positioned through a puncture in a liquid-carrying vessel, the lumen including a fluid outlet port and a guidewire exit port and including a distal opening forming both a distal fluid inlet port and a distal guidewire entry port, the distal fluid inlet port and the distal guidewire entry port being in fluid communication by an open neck portion disposed between the distal fluid inlet port and the distal guidewire entry port, the fluid outlet port and guidewire exit port being in fluid communication with the lumen, the shaft having a reduced-cross section region configured to allow the guidewire to exit the guidewire exit port and prevent passage of liquid through the guidewire exit port; and a trigger configured to simultaneously retract the locator from the puncture in the liquid-carrying vessel while effecting delivery of a closure device to close the puncture.

10. The surgical instrument of claim 9, wherein the trigger is located on a housing coupled to a proximal end of the shaft.

11. The surgical instrument of claim 9, the closure device disposed around the locator and having at least two tissue-penetrating legs formed thereon.

12. The surgical instrument of claim 11, wherein the at least two tissue-penetrating legs of the closure device are movable between a first, pre-deployed position, wherein the legs are substantially parallel to one another, and a second, deployed position wherein the legs extend toward one another.

13. The surgical instrument of claim 11, wherein the closure device is a staple.

14. A surgical instrument for closing a puncture wound, comprising:

a housing having an elongate shaft extending distally therefrom;

a member having a lumen configured to receive a guidewire, the lumen extending from a proximal end of the housing to a distal end of the member, the lumen including a fluid outlet port and a guidewire exit port and including a distal opening forming both a distal fluid inlet port and a distal guidewire entry port, the distal guidewire entry port of the opening having a diameter greater than a width of the distal fluid inlet port, the fluid outlet port and guidewire exit port being in fluid communication with the lumen, the member having a reduced-cross section region toward the guidewire exit port that is configured to allow the guidewire to exit the guidewire exit port and prevent passage of liquid through the guidewire exit port, the member extending from the housing and slidably movable with respect to the shaft between a forward position in which the member projects beyond a free end of the shaft to enter a puncture site in a liquid-carrying vessel and thereby locate the free end of the shaft at the puncture site, and a rearward position in which the member is retracted relative to the shaft; and a trigger located on the housing and effective to cause a closure device to advance through the elongate shaft and to cause the member to be substantially simultaneously retracted relative to the shaft such that the member is withdrawn from the closure device in time to allow the closure device to close the puncture site.

15. The surgical instrument of claim 14, the closure device having at least two forwardly pointing legs disposed on opposed sides of the member.

16. The surgical instrument of claim 15, wherein the at least two forwardly pointing legs are movable between a first pre-deployed position in which the legs are substantially parallel to one another, and a second deployed position in which the legs extend toward one another.

17. The surgical instrument of claim 14, wherein the member comprises a locator.

18. A surgical stapling apparatus, comprising:

a hollow shaft;

a member slidably receivable within the hollow shaft and movable between a forward position in which the member projects beyond a forward end of the hollow shaft to position the forward end of the hollow shaft over a puncture in a liquid-carrying vessel, and a rearward position in which the member is refracted relative to the hollow shaft, the member having a blood indicator lumen configured to deliver liquid from the liquid-carrying vessel toward a distal end to indicate position of the hollow shaft adjacent to the liquid-carrying vessel and receive a portion of a guidewire, the blood indicator lumen including a fluid outlet port having an opening that is smaller than a diameter of the guidewire, a guidewire exit port configured to receive the guidewire, and a distal opening in fluid communication with the blood indicator lumen, the distal opening forming both a distal fluid inlet port and a distal guidewire entry port, the distal guidewire entry port of the opening having a diameter greater than a width of the distal fluid inlet port, the distal fluid inlet port and the distal guidewire entry port being in fluid communication one with the other by an open neck portion disposed between the distal fluid inlet port and the distal guidewire entry port, the fluid outlet port and guidewire exit port being in fluid communication with the blood indicator lumen, with the fluid outlet port being distal the guidewire exit port, the member having a reduced-cross section region toward the guidewire exit port configured to allow the guidewire to exit the guidewire exit port and prevent passage of liquid through the guidewire exit port; and a trigger effective to drive a staple through the hollow shaft to staple together the puncture and simultaneously retract the member as the staple is released.

19. The surgical stapling apparatus of claim 18, wherein the member comprises a locator.

20. The surgical stapling apparatus of claim 18, wherein the member is adapted to be positioned between legs of a staple when the member is in the forward position.

21. The surgical stapling apparatus of claim 18, wherein the member is adapted to extend into a puncture in a liquid-carrying vessel when the member is in the forward position.

22. The surgical stapling apparatus of claim 18, wherein the trigger is coupled to a housing formed on a proximal end of the hollow shaft.

* * * * *